（12）United States Patent
Vincent et al.

(10) Patent No.: US 8,114,969 B2
(45) Date of Patent: Feb. 14, 2012

(54) IMMUNOTOXIN DERIVED FROM A RECOMBINANT HUMAN AUTOANTIBODY AND METHOD OF USING THEREOF

(75) Inventors: Angela Vincent, Wellington Square (GB); Alexander Marx, Wurzburg (GB); Stefan Gattenlohner, Wurzburg (GB)

(73) Assignee: ISIS Innovation, Ltd., Oxford (GB)

( * ) Notice: Subject to any disclaimer, the term of this patent is extended or adjusted under 35 U.S.C. 154(b) by 0 days.

(21) Appl. No.: 10/950,677

(22) Filed: Sep. 28, 2004

(65) Prior Publication Data

US 2006/0013809 A1 Jan. 19, 2006

Related U.S. Application Data

(60) Provisional application No. 60/507,131, filed on Oct. 1, 2003.

(51) Int. Cl.
*C07K 16/00* (2006.01)
*A61K 39/00* (2006.01)

(52) U.S. Cl. .................. 530/391.3; 424/178.1

(58) Field of Classification Search .......... None
See application file for complete search history.

(56) References Cited

U.S. PATENT DOCUMENTS 5,869,045 A * 2/1999 Hellstrom et al. ......... 424/130.1
6,657,103 B1 * 12/2003 Kucherlapati et al. ............ 800/6

OTHER PUBLICATIONS

Jacobson et al, J Neuroimmunol, 1999, 98:112-120.*
Heidenreich et al, Autoimmunity, 1988, 1:285-297.*
Marks et al, J Mol Biol, 1991, 222:581-597.*
Paul, Fundamental Immunology, 3rd Edition, 1993, pp. 292-295, under the heading "Fv Structure and Diversity in Three Dimensions".*
Rudikoff et al, Proc. Natl. Acad. Sci. USA, 79(6):1979-1983, Mar. 1982.*
MacCallum et al, J. Mol. Biol., 262, 732-745, 1996.*
Casset et al, Biochemical and Biophysical Research Communications, 307:198-205, 2003.*
Colman P. M., Research in Immunology, 145:33-36, 1994.*
Vajdos et al., Journal of Molecular biology, 2002, vol. 320, pp. 415-428.*
Holm et al, Molecular Immunology, 2007, vol. 44, pp. 1075-1084.*
Pascalis et al, Journal of Immunology, 2002, vol. 169, pp. 3076-3084.*

* cited by examiner

*Primary Examiner* — Misook Yu
*Assistant Examiner* — Mark Halvorson
(74) *Attorney, Agent, or Firm* — Pearl Cohen Zedek Latzer, LLP; Mark S. Cohen

(57) ABSTRACT

The invention is directed to an immunotoxin directed at fetal AchR, wherein the immunotoxin may comprises a human Fab fragment based on a human autoantibody or human combinatorial CDNA library and may be a pseudomonas exotoxin A-based single chain Fv IT (35-scFV-ETA). The invention is further directed to method of treating a patient with soft tissue tumor comprising the step of exposing the patient to the immunotoxin of the invention.

21 Claims, 18 Drawing Sheets

FIG. 10A

CDR1

| | 15 G GGG | 18 L CTG | 19 R AGA | 23 A GCA | 28 T ACC | 29 F TTC | 30 S AGT | 31 S AGC | 32 Y TAT | 33 S AGC | 35 N AAC | 38 R CGC | 39 Q CAG | 40 A GCT |
|---|---|---|---|---|---|---|---|---|---|---|---|---|---|---|
| VH3-21 | | | | | | | | | | | | | | |
| AMC-M6 10H | -A- E | --A | --- | -ATT I | --- | --T | -A- N | -C- T | --C | -AT N | --T | --T | --- | C-- P |
| AMC-M6 5H | -A- E | --A | --- | -ATT I | --- | --T | -A- N | -C- T | --C | -AT N | --T | --T | --- | C-- P |
| AMC-M6 6H | -A- E | --A | --G | CTT L | --- | --T | -A- N | -C- T | --C | -AT N | --T | --T | --- | C-- P |
| AMC-M6 2H | -AC D | -GA R | --G | -TT V | --T | --T | -AC N | -C- T | --C | -AT N | --T | --T | --- | C-- P |
| AMC-M6 4H | -A- E | --A | --- | -ATT I | --- | --T | -A- N | -C- T | --C | -AT N | --T | --T | --A | A-- T |
| AMC-M6 11H | -A- E | --A | --- | -TT V | --G | --T | -AC N | -C- T | --C | -A- N | --T | --T | --- | C-- P |

CDR2

| | 44 G GGG | 46 E GAG | 49 S TCA | 50 S TCC | 51 I ATT | 52 S AGT | 52a S AGT | 53 S AGT | 54 S AGT | 56 Y TAC | 57 I ATA | 58 Y TAC | 59 Y TAC |
|---|---|---|---|---|---|---|---|---|---|---|---|---|---|
| VH3-21 | | | | | | | | | | | | | |
| AMC-M6 10H | --C | --A | G-T A | --- | --A | -CA T | GCC A | -C- T | --C | C-- H | -C- T | G-G E | --- |
| AMC-M6 5H | --A | --A | G-T A | --A | --A | -CA T | GCC A | -C- T | --C | C-- H | -C- T | G-G E | --- |
| AMC-M6 6H | --A | --A | G-T A | --A | --A | -CA T | GCC A | -C- T | --C | C-- H | -C- T | G-G E | --- |
| AMC-M6 2H | --A | --A | G-T A | --A | --A | -CG T | TCG S | -C- T | --C | C-- H | -C- T | G-G E | --- |
| AMC-M6 4H | --A | --- | G-- A | --A | --A | --- T | -CG T | -C- T | --- | C-T H | -C- T | G-G E | --- |
| AMC-M6 11H | --C | --- | G-C A | --A | --A | -CA T | -CG T | -C- T | --C | C-T H | -C- T | G-G E | --T |

FIG.10B

CDR2 cont.

| | 60 A GCA | 61 D GAC | 62 S TCA | 63 V GTG | 64 K AAG | 65 G GGC | 66 R CGA | 68 T ACC | 74 A GCC | 76 N AAC | 77 S TCA | 78 L CTG | 80 L CTG | 81 Q CAA |
|---|---|---|---|---|---|---|---|---|---|---|---|---|---|---|
| VH3-21 | | | | | | | | | | | | | | |
| AMC-M6 10H | -G- | AG- S | --C | --T | GC- A | --A | --C | | A-- T | --G K | --T | --T | --A | G-C D |
| AMC-M6 5H | -G- | --G G | --C | --T | GC- A | --A | --C | | | --G K | --T | --T | --A | G-C D |
| AMC-M6 6H | -G- | --G G | --C | --T | GC- A | --A | --C | | A-- T | --G K | --T | --T | --A | G-C D |
| AMC-M6 2H | -G- | --G G | --C | --T | GC- A | | --C | | A-- T | --G K | --T | | | G-C D |
| AMC-M6 4H | A-- | | --C | --T | GC- A | --G E | --C | | A-- T | --G K | --T | --T | --A | G-C D |
| AMC-M6 11H | -G- | -G- G | --T | --T | GC- A | -AG | -G | -G- S | A-- | --G K | --C | | --A | G-C D |

| | 83 N AAC | 84 S AGC | 88 E GAG | 91 A GCT | 92 V GTG | 94 Y TAC |
|---|---|---|---|---|---|---|
| VH3-21 | | | | | | |
| AMC-M6 10H | -C- T | C-T R | --A | --A | C-T L | --T F |
| AMC-M6 5H | -C- T | C-T R | --A | --A | C-T L | -TT F |
| AMC-M6 6H | -C- T | C-T R | --A | --A | C-T L | -TT F |
| AMC-M6 2H | -C- T | C-T R | --- | --A | C-T L | -TT F |
| AMC-M6 4H | -C- T | | --A | --A | C-T L | --T F |
| AMC-M6 11H | -C- T | C-T R | --A | --A | C-T L | -TT F |

FIG. 10C

| | 10 S TCC | 11 L CTG | 13 A GCA | 15 V GTA | 16 G GGA | 18 R AGA | 20 T ACC | 21 I ATC | 22 T ACT | 27 Q CAG | 28 S AGC | 29 I ATT | 30 S AGC | 31 S AGC | 32 Y TAT | 33 L TTA |
|---|---|---|---|---|---|---|---|---|---|---|---|---|---|---|---|---|
| | | | | | | | | | | | | | CDR1 | | | |
| VK1 02/12 | | V | | P | | | | | S | E | | V | N | T | | |
| AMC-M6 10K | --- | G-- | --G | CCT P | --T | | --T | --T | T-- | G-- | -C- T | G-- V | -AT N | -CA T | --- | C-C |
| AMC-M6 5K | -T- T | --- | --G | CCT P | --T | --G | --T | --T | T-- S | G-- E | -C- T | G-- V | -AT N | -CA T | --- | C-C |
| AMC-M6 6K | A-- | --- | --G | C-T L | --- | --- | --T | --T | T-- S | G-- E | -C- T | --- | -AT K | -CA T | --- | --- |
| AMC-M6 2K | -T- T | --- | --- | C-T L | --- | --- | --T | --T | T-- S | --- | -C- T | --- | -AG D | -CA T | --- | --- |
| AMC-M6 4K | A-- | --- | --G | C-T L | --- | --- | --T | --T | T-- S | G-- E | -C- T | --- | GAT K | -CA T | --- | --- |
| AMC-M6 11K | --- | --- | --G | C-T L | --- | --- | --T | --T | T-- S | G-- | -C- T | --C | -AT N | TCA | N A-- | --- |

| | 34 N AAT | 36 Y TAT | 37 Q CAG | 38 Q CAG | 40 P CCA | 41 G GGC | 42 K AAA | 45 K AAG | 46 L CTC | 47 L CTG | 49 Y TAT | 50 A GCT | 53 S AGT | 55 Q CAA | 56 S AGT |
|---|---|---|---|---|---|---|---|---|---|---|---|---|---|---|---|
| | | | | | | | | | | | | CDR2 | | | |
| VK1 02/12 | | | | | | | | | V | | | S | T | | R |
| AMC-M6 10K | --C | --C | --A | --A | -AG Q | --A | -A | G-G E | G-- V | --A | --C | T-- S | -C- T | --- | -A R |
| AMC-M6 5K | --C | --C | --A | --A | -AG Q | --- | --- | G-G E | G-- V | --- | --- | T-- S | -C- T | --- | -A R |
| AMC-M6 6K | --- | --- | --A | --A | -A- | -A | --- | G-G E | G-- V | --- | -C- S | T-A S | -C- T | P-- | -A R |
| AMC-M6 2K | --- | --C | --A | -CA P | Q | --- | --- | G-G E | G-- V | --- | -C- H | T-- S | -C- T | -C- | -A R |
| AMC-M6 4K | --- | --- | --A | --A | -A- | -A | --- | G-G E | -V- | --- | -C- S | --A | -C- T | --- | -A R |
| AMC-M6 11K | --- | --- | --A | -CA P | Q | -A | --- | G-G E | G-- | --- | -C- | -A | --- | --- | -A R |

FIG.10D

| | 57 | 59 | 60 | 66 | 76 | 77 | 78 | 79 | 81 | 87 | 89 | 92 | 93 |
|---|---|---|---|---|---|---|---|---|---|---|---|---|---|
| | G | P | S | G | S | S | L | Q | E | Y | Q | Y | S |
| VK1 02/12 | GGG | CCA | TCA | GGA | AGC | AGT | CTG | CAA | GAA | TAC | CAA | TAC | AGT |
| AMC-M6 10K | -AC / D | --G | --G | --- | -C- / T | -A- / N | G-A / V | --G | --C / D | --T | --- | --T | --- / L / TTA |
| AMC-M6 5K | -AC / D | --G / S | --G | --- | -C- / T | -A- / N | --- | --G | --- | --- | --- | --- | --- / L / TTA |
| AMC-M6 6K | -AC / E | T-- | --G | --G | -A- / N | -A- / N | --- | --G | --- | --- | --- | --- | -C- / T |
| AMC-M6 2K | -A- / D | --- / S | --- | --- | -C- / T | -A- / N | --- | --G | --- | --- | --- | -TT / F | -CA |
| AMC-M6 4K | -AC / E | T-- | --G | --G | -A- / N | -A- / N | --- | --G | --- | --- | --- | --- | -C- / T |
| AMC-M6 11K | -AA | --- | --G | --- | --- | -A- | --- | --G | --- | --- | --- | --- | -C- / T |

EVOLUTION OF VH AND VK CLONES FROM AMC-M6. SEQUENCE ALIGNMENTS AND GENEALOGIC TREES FOR (A) AMC-M6 VH3-21 HEAVY CHAIN AND (B) VK1 02/12 KAPPA CHAIN GENES. THE FAB NUCLEOTIDE SEQUENCES WERE ALIGNED WITH THE BEST-MATCHING GERMLINE GENES. ONLY CODONS AT WHICH MUTATIONS OCCUR ARE SHOWN, AND ANY AMINO ACID CHANGES ARE INDICATED ABOVE. THE MOST PARSIMONIOUS GENEALOGIC TREES WERE DETERMINED ON THE BASIS OF SHARED AND UNSHARED MUTATIONS USING THE PAUP PROGRAM (SWOFFORD,1993). FAB NAMES ARE SHOWN IN CIRCLES, WITH H REFERRING TO THE HEAVY CHAIN AND K REFERRING TO THE KAPPA CHAIN. DOTTED CIRCLES REFER TO HYPOTHETICAL INTERMEDIATES. NUMBERS BESIDE ARROWS SHOW THE MINIMUM NUMBER OF SUBSTITUTIONS REQUIRED AT EACH STEP (WHICH MAY INCLUDE MULTIPLE CHANGES AT A SINGLE NUCLEOTIDE POSITION)

TABLE 1. CLINICAL DETAILS OF PAROUS MOTHERS

| AGE AT ONSET OF MG | No. CHILDREN AND TIME SINCE LAST BIRTH, AT ONSET OF MG | No. CHILDREN AT SAMPLING, AGE OF LAST CHILD | AGE AT SAMPLING | AChR TITER (nM)[a] | INHIBITION OF FETAL AChR FUNCTION (%) |
|---|---|---|---|---|---|
| 22 yr | 1 (NMG), postpartum | 1, 4 yr | 26 yr | 24.1 | 30 |
| 22 yr | 0, Before pregnancy | 1, 6 yr | 33 yr | 34.1 | 28 |
| 35 yr | 3, During pregnancy | 3, 2 yr | 36 yr | 2.4 | 24 |
| 27 yr | 2, Not known | 3, Not known | 29 yr | 24.0 | 22 |
| 25 yr | 1, 1 yr | 1, 3 yr | 26 yr | 19.9 | 15 |
| 39 yr | 2, Not known | 2, Not known | 41 yr | 10.6 | 4.5 |
| 30 yr | 1, 1 yr | 1, 1 yr | 31 yr | 14.2 | 3.8 |
| 31 yr | 1, 5 yr | 3, 2 yr | 38 yr | 25.9 | 3.4 |
| 29 yr | 1, Postpartum | 1, <1 yr | 29 yr | 10.2 | 3.2 |
| 32 yr | 2, Postpartum | 2, <1 yr | 33 yr | 40.1 | 2.3 |
| 29 yr | 2, During pregnancy | 3, 6 yr | 35 yr | 33.6 | 1.8 |
| 47 yr | 2, 21 yr | 2, 23 yr | 49 yr | 20.6 | 0 |

[a] THESE VALUES WERE THOSE OBTAINED IN ROUTINE SCREENING AND WILL BE UNDERESTIMATES IN SOME CASES.

FIG.11

TABLE 2. SCREENING AND DERIVATION OF THE ANTI-AChR Fab CLONES

| | No. OF CLONES SCREENED | SCREENING METHOD | No. OF POSITIVES OBTAINED | No. OF CLONES ISOLATED | MAIN CLONES CHARACTERIZED |
|---|---|---|---|---|---|
| AMC-M2 VH/Vκ | 2.5 × 10⁵ | ¹²⁵I-α-BuTx-AChR | 34 | 25ᵃ | 8H/K, 10H/K, 13H/K, 28H/K, 30H/K, 38H/K |
| AMC-M2 VH/Vκ | 2.5 × 10⁵ | AChR followed by ¹²⁵I-α-BuTx | 17 | 15 | 35H/K, 53H/K |
| AMC-M2 VH/Vλ | 2.5 × 10⁵ | ¹²⁵I-α-BuTx-AChR | 29 | 25ᵃ | NDᵇ |
| AMC-M6 VH/Vκ | 2.0 × 10⁵ | ¹²⁵I-α-BuTx-AChR | 13 | 10 | 1H/K, 2H/K, 4H/K, 5H/K, 6H/K, 8H/K, 10H/K, 11H/K |

ᵃPRELIMINARY BstXI DIGESTS OF THE VH/VL INSERTS SHOWED THAT ~80% OF THE CLONES WERE CLEARLY DIFFERENT; WE CHARACTERIZED AND SEQUENCED THOSE THAT GREW MOST READILY, AS ALSO WITH CLONES 35K AND 53K FROM THIS PATIENT AND WITH THOSE AMC-M6.

ᵇFOR AMC-M2 VH/Vλ, THE NINE COMPLETE VH SEQUENCES SHOWED NEAR IDENTITY TO THE VH3-07 GENES USED IN THIS PATIENT'S VH/Vκ CLONES, WHEREAS THE Vλ GENES WERE HETEROGENEOUS (NOT SHOWN).

FIG.12

TABLE 3. HEAVY AND LIGHT CHAIN V GENES ENCODING ANTI-AChR FABS

| | HEAVY CHAIN GENE | | | | | LIGHT CHAIN GENE | | | | | | |
|---|---|---|---|---|---|---|---|---|---|---|---|---|
| Fab | V$_H$–D$_H$–J$_H$ SEGMENTS | No. OF VH MUTATIONS | R:S RATIO FWR | R:S RATIO CDR | CDR3 LENGTH[a] | V$_k$–J$_k$ SEGMENTS | | No. of V$_H$ MUTATIONS | R:S ratio FWR | R:S ratio CDR | CDR3 LENGTH | AChR SPECIFICITY |
| AMC-M2 | | | | | | | | | | | | |
| 10H/K | VH3-07 D? JH6b | 33 | 1.0 | 12 | 23 | VK1 | L5 JK1 | 13 | 1.5 | 1.7 | 9 | Fetal |
| 13H/K | VH3-07 D? JH6b | 32 | 0.9 | 12 | 23 | VK1 | 02/12 JK4 | 33 | 0.9 | 1.7 | 9 | Fetal |
| 30H/K | VH3-07 D? JH6b | 32 | 0.9 | 12 | 23 | VK3 | L2 JK2 | 2 | – | >2 | 11 | Fetal |
| 28H/K | VH3-07 D? JH6b | 33 | 0.5 | 12 | 23 | VK1 | L1 JK1 | 2 | >1 | <1 | 9 | Fetal |
| 35H/K[b] | VH3-07 D? JH6b | 34 | 0.5 | 13 | 23 | VK2 | 02/12 JK1 | 3 | – | >3 | 11 | Fatal |
| 53H/K[b] | VH3-07 D? JH6b | 33 | 0.5 | 12 | 23 | VK1 | A3/19 JK4 | 11 | 1.0 | 1.3 | 9 | Fatal |
| 8H/K | VH3-07 D? JH6b | 34 | 0.6 | 12 | 23 | VK1 | 08/18 JK2 | 20 | 2.0 | 7.0 | 9 | Fetal |
| 38H/K | VH3-07 D? JH6b | 49 | 1.7 | 3.8 | 23 | VK1 | L11 JK1 | 10[c] | 2.0 | 1.3 | 8 | Fetal |
| AMC-M6 | | | | | | | | | | | | |
| 8H/K | VH4-61*02 DH1-26 JH4b | 36 | 1.0 | >14 | 10 | VK1 | 02/12 JK1 | 16 | 0.2 | >9 | 9 | Adult and Fetal |
| 1H/K | VH3-23 DH3-3 JH6b | 27 | 1.0 | 2.8 | 14 | VK4 | B3 JK3 | 14 | 1.0 | 3.0 | 9 | Fetal |
| 10H/K | UH3-21 D? JH5b | 55 | 0.8 | 2.1 | 18 | VK1 | 02/12 JK4 | 49 | 0.7 | 2.3 | 9 | Fetal |
| 5H/K | VH3-21 D? JH5b | 54 | 0.7 | 1.8 | 18 | VK1 | 02/12 JK4 | 44 | 0.6 | 2.3 | 9 | Fetal |
| 6H/K | VH3-21 D? JH5b | 55 | 0.8 | 1.8 | 18 | VK1 | 02/12 JK4 | 36 | 0.9 | 9.0 | 9 | Fetal |
| 2H/K | VH3-21 D? JH5b | 56 | 0.7 | 1.8 | 18 | VK1 | 02/12 JK4 | 34 | 1.0 | 9.0 | 9 | Fetal |
| 4H/K | VH3-21 D? JH5b | 48 | 0.7 | 1.3 | 18 | VK1 | 02/12 JK4 | 35 | 0.8 | 8.0 | 9 | Fetal |
| 11H/K | VH3-21 D? JH5b | 56 | 0.8 | 1.6 | 18 | VK1 | 02/12 JK4 | 31 | 0.8 | 4.0 | 9 | Fetal |

FIG.13A

|  | VH CDR3 amino acid sequence | VK CDR3 amino acid sequences |
|---|---|---|
| AMC-M2 | | |
| 10, 13, 30, 28, 35 and 53H/K | VRRYGPSTLSPFTWKDNHYAMD (SEQ ID NO: 13) | VK genes unrelated, all VK CDR3s are different |
| 38H/K | VRQFGALPPNQYNFDELHYAMD (SEQ ID NO: 14) | |
| AMC-M6 | | |
| 8H/K | GRGKFELLDF (SEQ ID NO: 15) | QQSYNTPNT (SEQ ID NO: 20) |
| 1H/K | VVNYQRSQVGWFDP (SEQ ID NO: 16) | QQYSGFSWT (SEQ ID NO: 21) |
| 10 and 5 H/K | EWGSRFITTFRGLPHFDL (SEQ ID NO: 17) | QQSYLTPLT (SEQ ID NO: 22) |
| 6 H/K | EWGSRFITTFRGLPHFDL (SEQ ID NO: 17) | QQSYTTPLT (SEQ ID NO: 23) |
| 2 H/K | EWGSRFITTFRGLPHFDL (SEQ ID NO: 17) | QQSFTTPLT (SEQ ID NO: 24) |
| 4 H/K | EWGSRFITSFRGLPHFDL (SEQ ID NO: 18) | QQSYTTPLT (SEQ ID NO: 23) |
| 11 H/K | EWGSRFITPFRGLPHFDL (SEQ ID NO: 19) | QQSYTTPLT (SEQ ID NO: 23) |

HEAVY AND LIGHT CHAIN V GENES ENCODING ANTI-AChR FABS FROM AMC-M2 AND AMC-M6. H/K REFERS TO THE HEAVY AND KAPPA V GENE SEQUENCES THAT HAVE BEEN DEPOSITED WITH GENBANK (ACCESSION NUMBERS AY033517-033550; SEQ ID NOS: 25-58).

a THE LENGTH OF THE CDR3 IS GIVEN IN AMINO ACIDS; THE CDR3 SEQUENCES ARE SHOWN IN THE BOTTOM HALF OF THE TABLE.

b ISOLATED BY SCREENING FIRST WITH UNLABELED AChR, FOLLOWED BY α-BuTx.

c THE 10 VK MUTATIONS DO NOT INCLUDE A THREE-BASE INSERTION AT THE END OF CDR1 AT AA35 THAT ENCODES A LEUCINE RESIDUE.

FIG. 13B

IMMUNOTOXIN DERIVED FROM A RECOMBINANT HUMAN AUTOANTIBODY AND METHOD OF USING THEREOF

CROSS REFERENCE DATA

This application claims the priority of Provisional U.S. Application No. 60/507,131 filed Oct. 1, 2003.

BACKGROUND OF THE INVENTION

Rhabdomyosarcomas (RMS), according to the WHO classification, comprise three types of tumours sharing skeletal muscle differentiation while showing distinct genetic and biological features: 1) embryonal with a characteristic loss of heterozygocity at 11p15; 2) the more aggressive alveolar, most of which show pathognomonic Pax3 or Pax7-FKHR fusion genes due to the translocations t(2;13)(q35;q14) and t(1;13)(p36;q14), respectively; and 3) the rare pleomorphic RMS with complex genetic aberrations and preferential occurrence in adults. As a group, RMS are the most frequent soft tissue tumour in children and have a poor prognosis. In particular, metastatic alveolar RMS in children more than 10 years old are often refractory to all current therapies including adjuvant bone marrow transplantation, resulting in 5-year survival rates of 5-20%. Immunotherapies or other (e.g. genetic) specific targeting strategies have not yet been applied due to the absence of a well defined RMS-specific gene target and the lack of suitable immunotherapeutic tools. However, it was shown previously that strong expression of fetal AChR mRNA and protein is virtually pathognomonic for non-innervated rhabdomyoblasts and rhabdomyotubes and, thus, for the vast majority of human embryonal and alveolar RMS; by contrast, fetal AChR expression is virtually absent in other tissues and in tumours without a rhabdomyoblast component.

The nicotinic AChR of skeletal muscle is a pentameric ion channel composed of five subunits. The fetal isoform is composed of $2\alpha$, $1\beta$, $1\gamma$ ad $1\delta$-subunits, while the adult isoform exhibits an $\epsilon$-subunit instead of the $\gamma$-subunit. During the later stages of development in uterus, the fetal AChR is gradually replaced by the adult isoform in virtually all innervated muscles. After birth, strong expression of fetal AChR is restricted to a few muscle fibres of unknown function occurring in extraoccular muscles and myoid cells of the thymus that are physiologically non-innervated muscle cells. However, high-level re-expression of fetal AChR can occur after birth following denervation, including denervating neuromuscular diseases.

In adult human innervated skeletal muscles, therefore, fetal AChR expression is exceedingly low. Only traces of $\gamma$-subunit mRNA can be detected by RT-PCR and RNAse protection assay, and very little by Northern blot. In addition, it has been shown that the mothers of newborns with arthrogryposis multiplex caused by the placental transfer of maternal antibodies specific to fetal AchR can be completely asymptomatic, suggesting that there is minimal expression of AChR $\gamma$-subunit protein on normal adult muscle.

Immunotoxins (ITs) are usually composed of a plant or bacterial toxin (like *Pseudomonas* exotoxin A=ETA) coupled to an antibody fragment for specific targeting of cells in the context of cancer, chronic inflammatory diseases, including autoimmune diseases and chronic infections, or transplantation. The antibody component of ITs is most often a murine Fab or Fv antibody fragment that has been humanised to minimize sensitization against the xenogeneic protein. Immunotoxins with a fully human antibody moiety (directed to HIV infected T-cells) have also been reported.

Impressive therapeutic efficacy of ITs has been demonstrated in a number of lymphomas and leukemias following short term application of the IT. By contrast, protracted use of an IT might be more adequate in poorly vascularized sarcomas. In such a clinical setting, is probably essential to minimize the sensitization against the mouse, rat or humanized antibody component of the IT.

Autoimmune disorders collectively cause much suffering and disability and many are particularly common in women of child-bearing age. The muscle weakness in the majority of myasthenia gravis (MG) patients results from autoantibodies to the acetylcholine receptor (AChR) which cause AChR loss, mainly by complement-mediated damage to the post-synaptic membrane and/or accelerated AChR degradation. The AChR consists of two $\alpha$ subunits and one $\beta$, $\gamma$ and $\delta$ in the fetus. Together, these subunits form a cation-specific ion channel that opens when ACh binds simultaneously to the two sites at the $\alpha/\delta$ and either the $\alpha/\gamma$ or $\alpha/\epsilon$ interfaces. From about 30 weeks' gestation in humans, the 'adult'-specific $\epsilon$ subunit gradually replaces the $\gamma$ subunit, but the fetal isoform continues to be expressed on rare myoid cells in the adult thymic medulla.

Early-onset MG (before age 40; EOMG) shows a ~3:1 female bias and a strong HLA-DR3-B8 association. The thymus is apparently an important site of autoimmunization; thymectomy is often beneficial and, in most EOMG cases, the thymus is invaded by lymph node-like T cell areas and germinal centers (GC, many of which show AChR-specificity. GC are well known sites of B cell memory generation and of antibody diversification by antigen-selection of somatic variants. Moreover, there is selective activation of thymic plasma cells spontaneously producing anti-AChR antibodies, with similar specificities to those in the patients' blood. The anti-AChR antibodies in typical MG patients are very heterogeneous and antibodies cloned from the thymus of typical EOMG patients show a range of specificities resembling those in the donors' sera.

About 8% of MG mothers have babies with transient neonatal MG, and their sera tend to have higher antibody titers against fetal than adult AChR, consistent with a role for thymic AChR in inducing their disease. In some rare examples, babies of MG mothers are born with severe developmental abnormalities, usually described as arthrogryposis multiplex congenita (AMC), which includes multiple joint contractures, hypoplasia of the lungs, other malformations and often fetal or neonatal death. The serum of these MG mothers, and others who are asymptomatic, contains antibodies that strongly and very selectively inhibit the ACh-triggered ion channel function of fetal AChR. These inhibitory antibodies persist in the maternal circulation and can transfer a similar condition to the pups after injection into pregnant mice. Interestingly, the first child of mothers of AMC babies is often unaffected and, when present, MG may not be clinically evident in the mother at the time of the first affected birth, suggesting that the maternal immune system may first be sensitized to AChR from the fetus. Moreover, the dominance of fetal AChR-specific antibodies in these women suggested that the B cell response might be clonally restricted.

Here we examined the relationship between inhibitory antibodies and parity in MG patients, and then took advantage of the fact that EOMG patients are treated by thymectomy, providing us with thymic B cells and plasma cells from which to clone and recombine fetal-AChR specific antibodies. We selected combinatorial Fabs from two MG mothers with high levels of fetal AChR-specific antibodies, whose babies had severe AMC. These Fabs proved to be strongly biased towards fetal AChR and were each dominated by one clone with extensive somatic diversification from an already highly mutated consensus sequence. These results suggest that the fetus could be responsible for immunizing the mother during pregnancy, with further diversification occurring subsequently in the thymus.

SUMMARY OF THE INVENTION

In one embodiment, the invention provides an immunotoxin directed at fetal AChR.

In another embodiment of the invention, the immunotoxin directed at fetal AChR further comprises a human Fab fragment based on a human autoantibody or human combinatorial cDNA library.

In another embodiment of the invention, the immunotoxin is a pseudomonas exotoxin A-based single chain Fv IT (35-scFV-ETA).

In another embodiment of the invention, the human Fab fragment of the immunotoxin is derived from a thymus cDNA library of a Myasthenia Gravis patient.

In another embodiment of the invention, there is provided a method of treating a patient with soft tissue tumour comprising the step of exposing the patient to the immunotoxin of the invention.

In another embodiment of the invention, there is provided a method of treating a patient with sarcoma comprising the step of exposing the patient to the immunotoxin of the invention.

In another embodiment of the invention the sarcoma is Rhabdomyosarcoma (RMS).

In another embodiment of the invention there is provided a method of killing cells comprising the step of contacting the cells with the immunotoxin of the invention.

In another embodiment of the invention, there is provided a method of delaying the development of RMS in a patient comprising the step of exposing the patient to the immunotoxin of the invention.

In another embodiment of the invention, there is provided a method of delaying the development of RMS cells, comprising the step of contacting the RMS cells with an immunotoxin of the invention.

In another embodiment, the invention provides a method of inducing immune tolerance in a recipient at risk of developing Myasthenia Gravis comprising the step of exposing the recipient to tolerogenic amount of fetal AChR, thereby inducing immune tolerance in a recipient at risk of developing Myasthenia Gravis.

In another embodiment, the invention provides a method of inducing immune tolerance in a recipient at risk of developing arthrogryposis multiplex congenita comprising the step of exposing the recipient to tolerogenic amount of fetal AChR, thereby inducing immune tolerance in a recipient at risk of developing arthrogryposis multiplex congenita.

In another embodiment, the invention provides a method of preventing Myasthenia Gravis in a recipient at risk of developing Myasthenia Gravis comprising the step of exposing the recipient to tolerogenic amount of fetal AChR, thereby inducing immune tolerance in a recipient at risk of developing Myasthenia Gravis.

In another embodiment, the invention provides a method of preventing arthrogryposis multiplex congenita in newborn of mothers with Myasthenia Gravis comprising the step of administering a tolerating amount of fetal AChR to mothers with Myasthenia Gravis or that are at risk of developing Myasthenia Gravis.

BRIEF DESCRIPTION OF THE DRAWINGS

FIG. 11 shows clinical details of the parous mothers.

FIG. 12 shows screening and derivation of anti-AchR Fab clones.

FIG. 13A presents an analysis of heavy and light chain V genes encoding anti-AchR Fabs from AMC-M2 and AMC-M6. H/K refers to the heavy and kappa V gene sequences that have been deposited with Genbank (Accession Numbers AY033517-033550; SEQ ID NOS: 25-58). The length of the CDR3 is given in amino acids.

FIG. 13B provides the CDR3 sequences (SEQ ID NOs: 13-24) from the heavy and light chain V genes encoding anti-AchR Fabs from AMC-M2 and AMC-M6.

DESCRIPTION OF THE DETAILED EMBODIMENTS OF THE INVENTION

Figure 2:
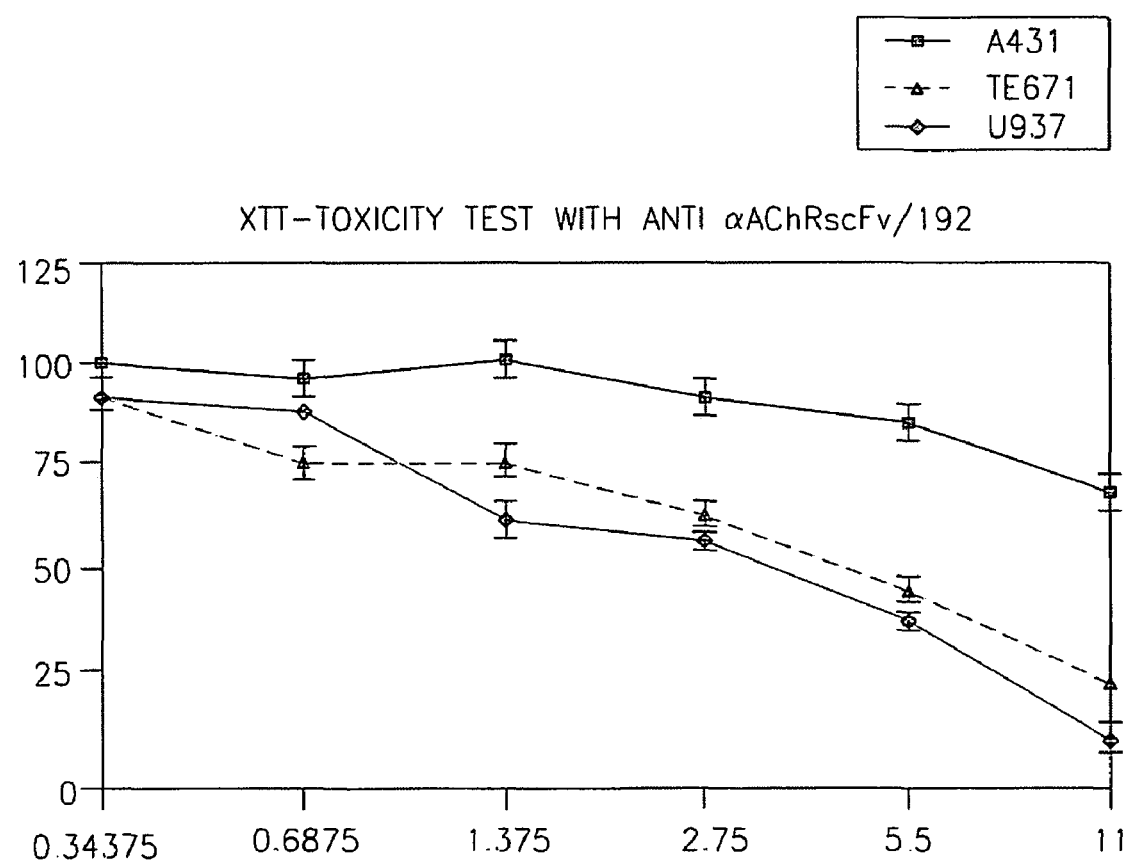
FIG. 2 demonstrates Colorimetric XTT cytotoxicity assay. Killing of TE671 RMS cells but not control cell lines (IMR32; A431; U937) in vitro by the IT scFv195-ETA that is a derivative of the rat monoclonal antibody mAb195.

Antibody-based immunotherapy is a well established therapeutic option in high-risk, ErbB2-positive breast cancer, lymphomas or leukemias. In a variety of other tumours, including colon and lung cancer, melanoma, Hodgkin lymphoma and neuroblastoma, immunotoxin-based strategies are being investigated. By contrast, sarcomas, including rhabdomyosarcomas, have not yet been targeted by immunotherapeutics in patients. This has been due to the lack of identified specific sarcoma antigens that are expressed at high levels at the surface of tumour cells but not on relevant normal tissues. In this respect, the description of the fetal AChR isofom as an abundant cell surface antigen of most RMS could be an advance: the invention provides the proof-of-principle that targeting the AChR by an immunotoxin is a feasible approach to kill RMS cells in vitro, while several control cell lines survived the treatment (FIG. 2). The experiments also imply that recombinant ligation of the truncated *Pseudomonas* exotoxin A (ETA) to the rat 195-scFv fragment and expression in bacteria, did not abrogate the affinity of the anti-AChR scFv moiety for the human AChR. In spite of its good in-vitro efficacy, 195-scFv-ETA is not suitable for use in animal models or patients because it targets the α-subunit that is shared by the adult and the fetal AChR. Therefore, it can be anticipated that 195-scFv-ETA will kill normal muscle fibers in addition to RMS, precluding its clinical usefulness.

Therefore, in one embodiment of the invention, there is provided a construction of an immunotoxin with specificity for the AChR γ-subunit and thus the fetal AChR isoform, the expression of which is close to nil in normal muscle. Two recombinant human Fab fragments that were shown previously to exhibit specific high affinity binding to the γ-subunit of the AChR, were used in the Examples, although the invention is not limited specifically to these Fab fragments. Surprisingly, only the scFv35VL-VH isoform but not the scFv35-VH-VL analogue, and none of the Fab38 derivatives exhibited significant binding to the fetal AChR.

In one embodiment, the invention provides an immunotoxin directed at fetal AChR. In another embodiment of the invention, immunotoxins are molecules that contain targeting domains that direct the molecules to target cells of interest (e.g., effector T lymphocytes, receptors, antigen on cancer cells) and toxic domains that kill the target cells. They are thus useful in pathological conditions such as, cancer, autoimmune diseases, and certain infectious diseases. The toxic domain can be, for example, any of the following toxic polypeptides: ricin, *Pseudomonas* exotoxin (PE), bryodin, gelonin, α-sarcin, aspergillin, restrictocin, angiogenin, saporin, abrin, pokeweed antiviral protein (PAP), or a functional fragment of any of these toxic polypeptides. The toxic domain can also be diphtheria toxin (DT) or a functional fragment thereof, e.g., a fragment containing amino acid residues 1-389 of DT.

In an embodiment of the invention, a toxic domain of a toxic polypeptide for use as a toxic domain in the fusion proteins of the invention is a fragment of the toxic polypeptide shorter than the full-length, wild-type toxic polypeptide but which has at least 5% (e.g., 10%, 20%, 30%, 40%, 50%, 60%, 70%, 80%, 90%, 95%, 99%, 100%, or even more) of the toxic activity of the full-length, wild-type toxic polypeptide. In vitro and in vivo methods for comparing the relative toxic activity of two or more test compounds are known in the art.

A target cell to which the immunotoxin of the invention binds can be a cancer cell, e.g., a a soft tumour cell, a sarcoma cell, a RMS cell, aneural tissue cancer cell, a melanoma cell, a breast cancer cell, a lung cancer cell, a gastrointestinal cancer cell, an ovarian cancer cell, a testicular cancer cell, a lung cancer cell, a prostate cancer cell, a cervical cancer cell, a bladder cancer cell, a vaginal cancer cell, a liver cancer cell, a renal cancer cell, a bone cancer cell, and a vascular tissue cancer cell.

In another embodiment of the invention, the immunotoxin directed at fetal AChR comprises a human Fab fragment based on a human autoantibody or human combinatorial cDNA library.

In another embodiment of the invention, the immunotoxin (IT) is a pseudomonas exotoxin A-based single chain Fv IT (35-scFV-ETA).

In another embodiment of the invention, the human Fab fragment of the immunotoxin is derived from a thymus cDNA library of a Myasthenia Gravis patient.

In an embodiment of the invention, "antibody fragments" or "Fab fragment" refers to antigen-binding fragments, e.g., Fab, F(ab')$_2$, Fv, and single chain Fv fragments.

The Fab fragment may be shorter than the full-length, wild-type targeting polypeptide but which has at least 5% (e.g., 10%, 20%, 30%, 40%, 50%, 60%, 70%, 80%, 90%, 95%, 99%, 100%, or even more) of the ability of the full-length, wild-type targeting polypeptide to bind to its relevant target molecule. The Fab or single chain fragment could also be part of a bi-valent or multi-valent or bi-specific or multi-specific targetting construct. Methods of comparing the relative ability of two or more test compounds to bind to a target molecule are well-known to artisans in the field, e.g., direct or competitive ELISA.

Figure 5:
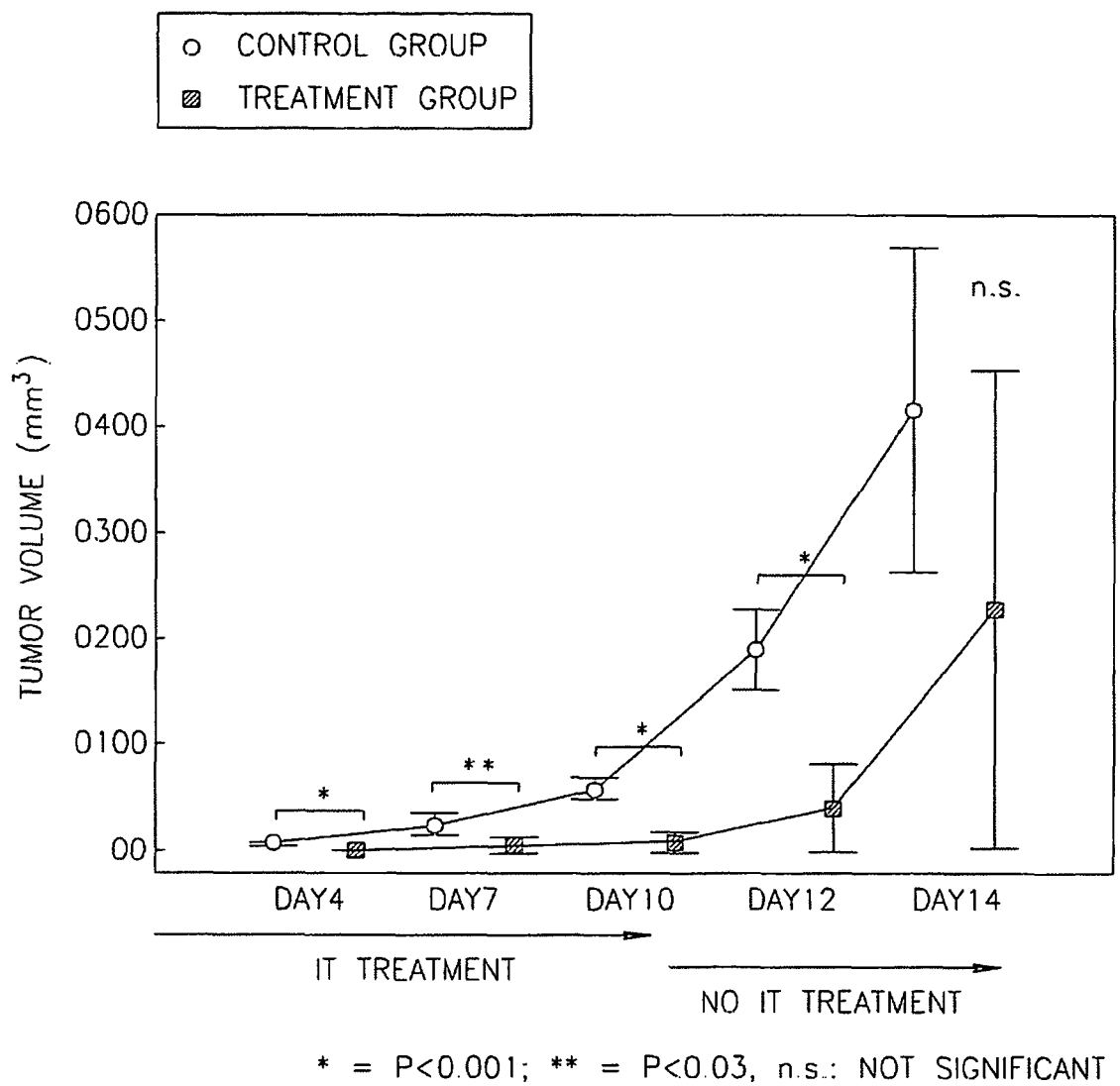
FIG. 5 demonstrates the effect of the immunotoxin treatment on the tumour volume in a mouse transplantation model.

The scFv35VL-VH-ETA IT was functionally effective both in vitro (FIG. 3) and in a mouse model in vivo (FIG. 5). The IT effect on RMS cells in vitro was specific, since control cell lines were not killed. In addition, the IT was not toxic in the 10 mice treated at a dose of 20 μg per day. There were several motifs to use a recombinant human Fab fragment derived from a thymus cDNA library of a Myasthenia gravis (MG) patients as the targeting moiety of the RMS-directed immunotoxin: (a) there were no easily available and well characterized mouse or rat monoclonal antibodies with anti-γ-subunit specificity; (b) human anti-AChR autoantibodies from MG patients are known for their high affinity and specificity that are often maintained in recombinant Fab or single chain Fv derivatives; (c) a human monoclonal autoantibody fragment as the targeting moiety of an immunotoxin is likely to be less immunogenic than a humanized mouse or rat antibody; (d) a human scFv offers the perspective to be applicable in a fully humanized immunotherapeutic agent, be it an immunotoxin (e.g. by using human ribonucleases or linked to other human effectors (e.g. interleukins, chemokines, T-cell receptor fragments, NK-cell receptor fragments, myeloid or dendritic cell signalling molecules).

The latter considerations (i.e. alternative applications of scFv35-derivatives) are likely to be of major practical importance considering both the cohesive growth of RMS in the clinical setting and the results of our in vivo experiments. As shown in FIG. 5, the "single agent" in-vivo treatment of mice with 35-scFv for 10 days did not cure the animals, since tumour growth was significantly delayed as long as the IT was administered but not totally blocked. In particular, the RMS cells already started to form small but palpable tumours while the IT treatment was still underway (tumour volumes 8+/−7 mm$^3$ as compared to 59+/−9 mm$^3$ in the untreated animals; FIG. 5). This observation suggests that some type of resistance to the treatment had occurred. While our preliminary immunohistochemical studies suggest, that downregulation of fetal AChR surface expression on RMS cells may not be the underlying mechanism, more studies are required to exclude this and other mechanisms that my cause IT resistance. Among the known mechanisms leading to IT resistance, poor vascularisation in sarcomas compared to leukemias or lymphomas almost certainly plays an important role. As to this problem, more prolonged and dose-escalated use of the IT could be one of the options to improve tumour control due to better penetration of the IT to the tumour. Considering the perspective of long-term treatment in humans, the possibility to derive a less toxic and minimally immunogenic, fully humanized IT on the basis of the scFv35 and a human toxin moiety appears desirable.

Figure 7:
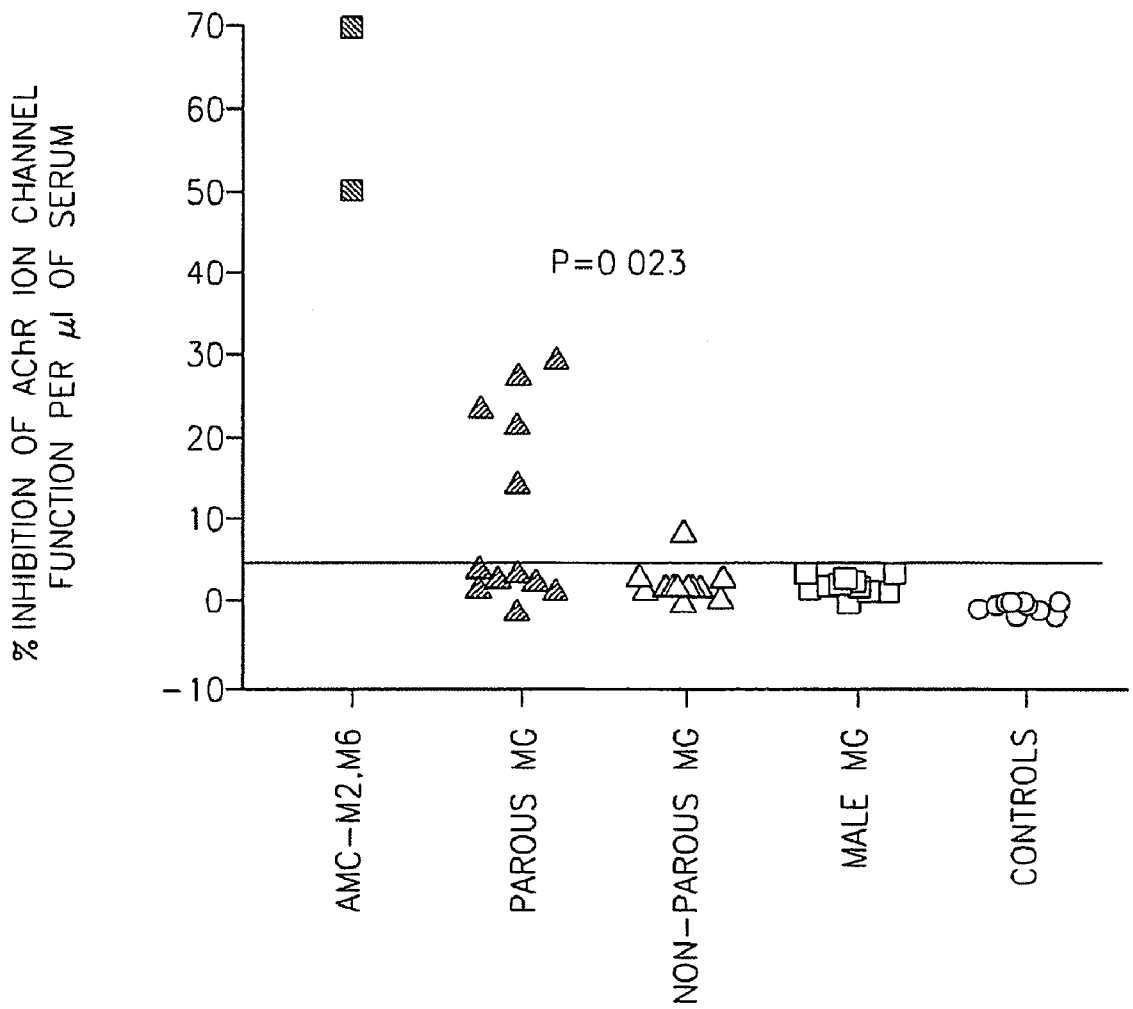
FIG. 7 shows the inhibition of fetal acetylcholine receptor (AchR) function by sera from AMC-M2 and AMC-M6 from different groups of patients with Myasthenia gravis and healthy controls.

In addition to dose escalation and extending treatment duration, other possibilities can already been forseen to improve the treatment of RMS with scFv35-based ITs (or other scFv35 derivatives). First, there are now well established molecular biological techniques to stabilize ITs, increase their affinity, and improve their internalization rate into tumour cells. Second, it becomes more and more obvious, e.g. in breast cancer, that single-agent antibody-based therapies as applied here in an experimental setting (FIG. 5) can be made more efficient when combined with "traditional" chemotherapies or targeted application of cytokines, chemokines, antiangiogenic agents or modifiers of degradation pathways that inactivate toxins. Third, as shown in leukemias, the therapeutic effect of ITs can be improved when the expression level of the target antigen and the percentage of target-positive tumour cells is elevated pharmacologically. All startegies appear likely applicable to RMS and scFv35VL-VH-ETA: as shown for a single RMS case previously and for another three new cases here, chemotherapy can drive the differentiation of immature, $AChR^{low}$ RMS cells to more mature rhabdomyoblasts with increased expression of muscle specific proteins, including fetal AChRs (FIG. 7) and Ref. Thus synchronous or metachronous application of chemotherapy and a fetal AChR IT appears reasonable for testing once the IT has been optimized.

In another embodiment of the invention, there is provided a method of treating a patient with sarcoma comprising the step of exposing the patient to the immunotoxin of the invention. The step of exposing may be either by oral, topical or by injection.

In another embodiment of the invention the sarcoma is Rhabdomyosarcoma (RMS).

In another embodiment of the invention there is provided a method of killing cells comprising the step of contacting the cells with the immunotoxin of the invention.

The step of contacting is by either direct administration to the cells or to the media which surround the cells.

In another embodiment of the invention, there is provided a method of delaying the development of RMS in a patient comprising the step of exposing the patient to the immunotoxin of the invention.

In another embodiment of the invention, there is provided a method of delaying the development of RMS cells, comprising the step of contacting the RMS cells with an immunotoxin of the invention. As can be seen in the examples section, a recombinant ETA-based immunotoxin derived from one of the human autoantibody fragments killed human RMS cells in vitro and resulted in a significant delay of tumour development.

In another embodiment of the invention, the method of treating and/or of killing a cell, and/or of delaying the development of a tumour further comprising a step of contacting or exposing the cells to a chemotherapeutic agent.

The chemotherapeutic agent is selected from the group consisting of a DNA-interactive agent, alkylating agent, antimetabolite, tubulin-interactive agent, hormonal agent, Asparaginase and hydroxyurea or without limitation from the group consisting of Asparaginase, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole carbamate and Plicamycin In summary, the invention shows that the fetal AChR is the so far most specific and potentially useful target antigen of human RMS to be recognized by an immunotoxin. The IT (Immunotoxin) described here (scFv35VL-VH-ETA) was effective both in vitro and in vivo against RMS cell lines. It is the first sarcoma directed agent based on a fully human autoantibody fragment. ScFv35VL-VH-ETA is a promising candidate for further preclinical testing, including its molecular modification towards better stability in vivo, higher binding affinity and coupling of human toxins or other effectors like cytokines or chemokines.

Rhabdomyosarcoma (RMS) or other tumour with rhabdomymatous differentiation is the leading malignant soft tissue tumour in children with high mortality rates in spite of modern multimodality treatments. Since strong expression of the γ-subunit of the acetylcholine receptor (AChR), defining the human fetal-type AChR isoform, is virtually specific for rhabdomyoblasts, RMS cells could be killed by immunotoxin (IT) directed at the fetal AChR. Two fully human Fab-fragments with specificity for fetal AChR, obtained from a combinatorial library created from a cDNA library derived from the thymus of a myasthenia gravis patient, and generated a pseudomonas exotoxin A-based single chain Fv IT (35-scFV-ETA). 35-scFV-ETA killed human embryonal and alveolar RMS cell lines in vitro and delayed RMS development after transplantation into mice. 35-scFV-ETA was specific to fetal AChR since it did not kill AChR-negative cell lines or HEK cells transfected with RNA for human adult-type AChRs indicating that it should not affect AChRs at the normal muscle endplates. 35-scFv-ETA is the first cancer-directed immunotoxin with a fully human antibody moiety and the first IT targeting an antigen that is virtually specific for RMS. 35-scFv-ETA appears promising for further preclinical evaluation as a therapeutic tool against high-risk RMS.

The invention shows, for the first time, that antibodies inhibiting the ion channel function of fetal AChR are common not only in mothers of AMC babies (Riemersma et al 1997), but also in women who developed MG after pregnancy. By contrast, such antibodies were uncommon in women who presented before pregnancy. In addition, the many high affinity Fabs that was cloned from the thymus of two AMC mothers showed a very strong preference for fetal AChR and a biased usage of VH3 genes. The striking diversification of the Fabs in each woman from a common, but already highly mutated, germ-line sequence, shows that the autoantibodies can arise via successive rounds of antigen-driven selection in a few clones. These results suggest a scenario in which oligoclonal responses to fetal AChR, including some that are fetal AChR inhibitory, are the initiating event in women who develop MG after pregnancy, irrespective of whether the extent of fetal AChR inhibitory antibodies is sufficient to cause AMC. Immunization by the fetus is, therefore, another contributory factor to the female bias evident in many autoimmune diseases, in addition to the established hormonal influences and the possible roles of fetal-maternal microchimerism.

The Fabs that were cloned from the two unrelated AMC-mothers show remarkable similarities. They clearly have high affinities, since they immunoprecipitate AChR at ~500 pM and, despite being monomeric, they also efficiently block binding of bivalent mAbs. In theory, the predominance of fetal AChR in the ischemic muscle extracts that were used might have created a bias in screening towards fetal AChR-binding Fabs. However, the MIR on the α subunits is thought to be the target of the majority of AChR antibodies in MG; although some may have a preference for the fetal isoform, it was possible to detect them with adult AChR, and to inhibit them with the anti-MIR mAb.

The efficient screening and cloning of Fabs binding specifically to fetal AChR implies a striking dominance of this specificity in the AMC mothers' thymic cells. Furthermore, it was shown a single dominant family of clonally related Vκ sequences in AMC-M6 and of VH3 sequences in both patients. In AMC-M2, the same clonally related VH3-07 sequences predominated whether they were isolated together with κ or λ light partners and irrespective of the screening procedure used (Table 2). A parallel restriction in Fabs recognizing a minority epitope, contrasting with heterogeneity of those against a dominant region, has recently been reported for thyroid peroxidase in a patient with Graves' disease. The VH3 germline genes of our two clonal families are both commonly used by normal blood B cells, as is the Vκ1 02/12 that predominated in AMC-M6 and recurred in AMC-M2. A PCR bias seems very unlikely since the five non-specific Fabs isolated from our AMC-M2 VH/Vκ library did not include the VH3-07, VH3-21 or Vκ1 02/12 genes, and VH3 genes are not over-represented in Fabs cloned, using the same primers, from autoimmune thyroid tissue.

Since the dominant VH3-07 used by AMC-M2 was paired with so many unrelated light chains (both κ and λ), its VH probably makes the major contribution to binding specificity, as has frequently been observed with other antibodies. With AMC-M6, by contrast, the recurring usage of highly mutated and clonally related light chains in exclusive combination with the dominant VH3-21 suggests that they also have a major influence on specificity. There are long-established precedents for that in certain heritable restricted responses in mice to well defined epilopes, and also in human autoantibodies.

Importantly, the deduced ancestral sequence for each of the dominant families is already highly mutated (with 32, 44 and 25 shared differences from germline for AMC-M2 and AMC-M6 VH, and AMC-M6 Vκ respectively) indicating that the progenitor B cells had already undergone antigen-selection in GC before further refinement in the thymus. Almost all of the present sequences show multiple mutations, especially in the CDRs where replacement: silent ratios were often high. Of particular interest is the evidence of convergent mutations in the two patients' VH and especially in the recurrent $^{22}$SRASET$^{28}$ sequences in Vκ, suggesting that these Fabs may be recognizing a dominant fetal AChR epitope. Together with the abundant mutations, the high R:S ratios in the CDRs, and the branching patterns of their evolution, these results strongly suggest that each Fab is the end-product of successive stages of antigen-driven clonal proliferation in GC, as also found after *Haemophilus* vaccination in subjects with preexisting B cell memory. One can envisage that, over the preceding years, and four and two pregnancies respectively, the memory B cells that were initially generated could re-activate and/or re-enter GC for further rounds of mutational refinement. The striking patterns of oligoclonal evolution/diversification that was have observed in the fetal AChR-specific Fabs from both AMC mothers, are very reminiscent of those noted in a mouse model with spontaneous SLE, where a surprising variety of specificities stemmed from remarkably few ancestral B cells.

Amino acid sequences of human anti-AChR Fab VH and Vκ Complimentarity Determining Region 3 (CDR3) of AMC-M2 and AMC-M6 are presented in FIG. 13B. In one embodiment, an anti-AChR Fab VH CDR3 of AMC-M2 of this invention has an amino acid sequence, which corresponds to VRRYGPSTLSPFTWKDNHYAMD (SEQ ID NO 13). In one embodiment, an anti-AChR Fab VH CDR3 of AMC-M2 of this invention has an amino acid sequence, which corresponds to VRQFGALPPNQYNFDELHYAMD (SEQ ID NO 14).

In one embodiment, an anti-AChR Fab VH CDR3 of AMC-M6 of this invention has an amino acid sequence, which corresponds to GRGKFELLDF (SEQ ID NO 15). In one embodiment, an anti-AChR Fab VH CDR3 of AMC-M6 of this invention has an amino acid sequence, which corresponds to VVNYQRSQVGWFDP (SEQ ID NO 16). In one embodiment, an anti-AChR Fab VH CDR3 of AMC-M6 of this invention has an amino acid sequence, which corresponds to EWGSRFITTFRGLPHFDL (SEQ ID NO 17). In one embodiment, an anti-AChR Fab VH CDR3 of AMC-M6 of this invention has an amino acid sequence, which corresponds to or is homologous to EWGSRFITSFRGLPHFDL (SEQ ID NO 18). In one embodiment, an anti-AChR Fab VH CDR3 of AMC-M6 of this invention has an amino acid sequence, which corresponds to EWGSRFITPFRGLPHFDL (SEQ ID NO 19).

In one embodiment, an anti-AChR Fab Vκ CDR3 of AMC-M6 of this invention has an amino acid sequence, which corresponds to QQSYNTPNT (SEQ ID NO 20). In one embodiment, an anti-AChR Fab Vκ CDR3 of AMC-M6 of this invention has an amino acid sequence, which corresponds to QQYSGFSWT (SEQ ID NO 21). In one embodiment, an anti-AChR Fab Vκ CDR3 of AMC-M6 of this invention has an amino acid sequence, which corresponds to QQSYLTPLT (SEQ ID NO 22). In one embodiment, an anti-AChR Fab Vκ CDR3 of AMC-M6 of this invention has an amino acid sequence, which corresponds to QQSYTTPLT (SEQ ID NO 23). In one embodiment, an anti-AChR Fab Vκ CDR3 of AMC-M6 of this invention has an amino acid sequence, which corresponds to QQSFTTPLT (SEQ ID NO 24).

Nucleotide sequences for coding sequences for the human heavy and light chain V genes encoding human anti-AChR Fabs of this invention are listed in FIG. 13B as GENBANK accession numbers AY033517-033550. In one embodiment, coding sequence of a heavy chain V gene of this invention, encoding anti-AChR Fabs from AMC-M2, has nucleotide sequence, which corresponds to gagtctgggggcgacttggtccagc-cgggggggtccctgagagtctcctgtg-tagcctctggatttacatttaggacctatgtgatgaa ctgggtccgccaggctccag-gaaaggggctggagtgggtggcccacataagtccagagggaactgaagaatact-atgcggactctg tgaagggccgatttaccatctccagaga-caacgcggagaattcagtatttctg-caaatgaacagtctgagaggcgaggacacggctgt gtattattgcgcgagagtc-cgacgctatggtccctctacactcagtccgttcacctggaaggacaatcactacgc-catgacgtctggg gccaagggaccacggtcaccgtctcttca (SEQ ID NO 25). In one embodiment, coding sequence of a heavy chain V gene of this invention, encoding anti-AChR Fabs from AMC-M2, has nucleotide sequence, which corresponds to gagtctgggggcgacttggtccagccgggg gggtccctgagagtctcctgtg-tagcctctggatttacatttaggac-ctatgtgatgaactgggtccgccaggctccaggaaaggggct ggagtgggtg-gcccacataagtccagagggaactgaagaatactatgcggactctgtgaagggcc-gatttaccatctccagagacaa cgcgaagaattcagtatttctgcaaat-gaacagtctgagaggcgaggacacggct-gtgtattattgcgcgagagtccgacgctatggtc cctctacactcagtccgttcac-ctggaaggacaatcactacgccatgacgtctggggccaagggaccacggtcac-cgtctcttca (SEQ ID NO 26). In one embodiment, coding sequence of a heavy chain V gene of this invention, encoding anti-AChR Fabs from AMC-M2, has nucleotide sequence, which corresponds to gagtctgggggcgacttggtccagc-cgggggggtccctgagagtctcctgtgtagcctctggatttacat ttaggacctat-gtgatgaactgggtccgccaggctccag-gaaaggggctggagtgggtggcccacataagtccagagggaactgaa gaatactatgcggactctgtgaagggc-cgatttaccatctccagagacaacgc-gaagaattcagtatttctgcaaatgaacagtctgag aggcgaggacacggctgtg-tattattgcgcgagagtccgacgctatggtccctctacactcagtccgttcacctgga-aggacaatcact acgccatggacgtctggggccaagggac-cacggttaccgtctcttc a, (SEQ ID NO 27). In one embodiment, coding sequence of a heavy chain V gene of this invention, encoding anti-AChR Fabs from AMC-M2, has nucleotide sequence, which corresponds to gagtcgggggcgacttggtcagccg Ggggggtccctgagagtctcctgtgtagcctctggatttacatttaggac-ctatgtgatgaactgggtccgtcaggctccaggaaagggctggagtgggtggcccacataagtcca-gagggaactgaagaatactatgcg-gactctgtgaagggccgatttaccatctccagaga caacgcgaagaattcagtatttctgcaaatgaacagtctgagaggcgaggacacggctgtgtattattgcgcg-agagtccgacgctat ggtccctctacactcagtccgttcac-ctggaaggacaatcactacgccatg-gacgtctggggccaagggaccacggtcaccgtctctt ca (SEQ ID NO 28). In one embodiment, coding sequence of a heavy chain V gene of this invention, encoding anti-AChR Fabs from AMC-M2, has nucleotide sequence, which corresponds to gagtcggggggcgacttggtccagc-cgggggggtccctgagagtctcctgtgtagcctctggatttacat ttaggacctat-gtgatgaactgggtccgccaggctccag-gaaagggctggagtgggtggcccacataagtccagagggaactgaa gaatactatgcggaccctgtgagggc-cgatttaccatctccagagacaacgc-gaagaattcagtatttctgcaaatgaatagtctgag aggcgaggacacggctgtg-tattattgcgcgagagtccgacgctatggtccctctacactcagtccgttcacctgg-aaggacaatcact acgccatggacgtctggggccaaggga-caacggtcaccgtctctcca (SEQ ID NO 29). In one embodiment, coding sequence of a heavy chain V gene of this invention, encoding anti-AChR Fabs from AMC-M2, has nucleotide sequence, which corresponds to gagtcggggggcgacttggtccagc-cgggggggtccctgagagtctcctgtg-tagcctctggatttacatttaggacctatgtgatgaa ctgggtccgccaggctccag-gaaagggctggagtgggtggcccacataagtccagagggaactgaagaatac-tatgcggactctg tgaagggccgatttaccatctccagaga-caacgcgaagaattcagtatttctg-caaatgaatagtctgagaggcgaggacacggctgt gtattattgcgcgagagtc-cgacgctatggtccctctacactcagtccgttcacctggaaggacaatcactacgc-catggacgtctg gggccaagggacaacggtcaccgtctctca (SEQ ID NO 30). In one embodiment, coding sequence of a heavy chain V gene of this invention, encoding anti-AChR Fabs from AMC-M2, has nucleotide sequence, which corresponds to gagtcggggggcgacttggtccagc-cgggggggtccctgagagtctcctgtg-tagcctctggatttacatttaggacctatgtgatgaa ctgggtccgccaggctccag-gaaagggctggagtgggtggcccacataagtccagagggaactgaagaatac-tatgcggactctg tgaagggccgatttaccatctccagaga-caacgcgatgaattcagtatttctg-caaatgaatagtctgagaggcgaggacacggctgtg tattattgcgcgagagtc-cgacgctatggtccctctacactcagtccgttcacctggaaggacaatcactacgct-atggacgtctg gggccaagggacaacggtcaccgtctctcca (SEQ ID NO 31). In one embodiment, coding sequence of a heavy chain V gene of this invention, encoding anti-AChR Fabs from AMC-M2, has nucleotide sequence, which corresponds to gagtcgggggaggcgtggtccagc-cgggggggtccctgacagtctcctg-taaagcctctggatatgttttcaggacctttctcatgac ttgggtccgcctggctc-caggaggggggctggagtgggtggccaacataagtccagcggggaactgagaa-acattatatggactctgt tgaggggcgattctccatctccagaga-caatgcccagaactcactcttctg-caaatgaacggcctgagaggcgaagacacggctctc tattttttgtgccagagtc-cgacaatttggtgcccttcctcccaatcaatataactttgatgaactccactacgcga-tggacctctgggggcca agggaccgcggtcatcgtctcctca (SEQ ID NO 32). In one embodiment, coding sequence of a heavy chain V gene of this invention, encoding anti-AChR Fabs from AMC-M2, has nucleotide sequence, which corresponds to gagtcgggggcgacttggtccagc-cgggggggtccctgagagtctcctgtg-tagcctctggatttacatttaggacctatgtgatgaa ctgggtccgccaggctccag-gaaagggctggagtgggtggcccacataagtccagcggggaactgaagaatac-tatgcggactctg tgaagggccgatttaccatctccagaga-caatgcccagaactcactcttctg-caaatgaacggcctgagaggcgaagacacggctct ctattttttgtgccagagtc-cgacaatttggtgcccttcctcccaatcaatataactttgatgaactccactacgcga-tggacctctgggggcc aagggaccgcggtcatcgtctcttca (SEQ ID NO 33).

In one embodiment, coding sequence of a light chain V gene of this invention, encoding anti-AChR Fabs from AMC-M2, has nucleotide sequence that corresponds to gagtcgtgat-gacccagtctccatcttccgtgtctg-tatctctaggagacagaatcaccatcacttgtcncgcgagtcaaaatattagca actggttagcctggtatcagcagaaac-cagggaaagcccctaagctcctgatc-tattctgcatccagtttgcaaagtggagtccatcaa ggttcagcg-gcagtgggtctgggacagatttcactctcaccatcagcagcctgcagcctgaagat-tttgcaacttactattgtcaacagc taacagtttcccccggacgttcggc-caagggaccaaggtggaaatcaaac (SEQ ID NO 42). In one embodiment, coding sequence of a light chain V gene of this invention, encoding anti-AChR Fabs from AMC-M2, has nucleotide sequence that corresponds to gagtcgtgatgac-ccagtctccatctccctgtctgcttct-gttggggacagaataaccatctcttgccgggcaagtgagaccattagt cattact-taaattggtatcagcagaatccagggaaagccccaaagctcctgatctttggtcat-ccacttggagagtgtgggtccctca aggttcagtggcgatggatctgggaca-gatttcactctcaccatcgacagcctc-caacctgaagattttgcaacgtactactgtcaacag ggttacagttcttcgct-cactttcggcggagggaccaaggtggagattaaag (SEQ ID NO 43). In one embodiment, coding sequence of a light chain V gene of this invention, encoding anti-AChR Fabs from AMC-M2, has nucleotide sequence that corresponds to gagtcgtgatgac-ccagtctccagccacccctgtctgt-gtctccaggggaaagagccaccctctcctgcagggccagtcagagtgttg cag-caacttagcctggtaccagcagaaacctggccaggctcccaggctcctcatctat-ggtcatccaccagggccactggtatcca gccaggttcagtg-gcagtgggtctgggacagagttcactct-caccatcagcagcctgcagtctgaagattttgcagtttattactgtcatc agtataataactggcttcggaaana-cacttttggccaggggaccaagctggagatcaaac (SEQ ID NO 44). In one embodiment, coding sequence of a light chain V gene of this invention, encoding anti-AChR Fabs from AMC-M2, has nucleotide sequence that corresponds to gagtcgtgatgaca-cagtctccatcctcactgtctgcatctg-taggagacagagtcaccatcacttgtcgggcgagtcagggcattag caattatt-tagcctggtttcagcagaaaccagggaaagcccctaagtcctgatctatgctgca-tccagtttgcaaagtggggtcccatc aaagttcagcggcagtggatctgggaca-gatttcactctcaccatcagcagcctg-cagcctgaagattttgcaacttattactgccaaca gtataatagttacccgatcacnt-tcggccaagggaccaaggtggaaatcaaac (SEQ ID NO 45). In one embodiment, coding sequence of a light chain V gene of this invention, encoding anti-AChR Fabs from AMC-M2, has nucleotide sequence that corresponds to gagtcgtgatgac-ccagtctccatcctccctgtctgcatct-gtaggagacagagtcaccatcacttgccgggcaagtcagaccattag caactatt-taaattggtatcagcagaaaccagggaaagcccctaagtcctgatctatggtgca-tccagtttgcaaagtggggtcccatc aaggttcagtggcagtggatctgggaca-gatttcactctcaccatcagcagtctg-caacctgaagattttgcaacttactactgtcaacag agttcagtaccctccgacg-tacacttttggcaggggaccaagctggagatcaaac (SEQ ID NO 46). In one embodiment, coding sequence of a light chain V gene of this invention, encoding anti-AChR Fabs from AMC-M2, has nucleotide sequence that corresponds to gagtcgtgatgac-ccagtctccactctccctgcccgtca-cacctggagagccgcctccatctcctgcaggtctagtcagagcctcc agca-gagtaatggacacaactatttgaattggtacctgcagaagccagggcagtccac-agttcctgatccacttgggttctaatcggg cctccggggtccctgacaggt-tcagtggcagtggatcaggcacagattt-tacactgaaaatcagcagagtggaggctgaggatgttgg ggtttattactgcatgcaggctctacaaaccccgctcactttcggcggagggaccaaggtggaaatcaaac (SEQ ID NO 47). In one embodiment, coding sequence of a light chain V gene of this invention, encoding anti-AchR Fabs from AMC-M2, has nucleotide sequence that corresponds to gagctcgtgatgacccagtctccatc-ctccctgtctgcatctgtaggagaca-gaatcaccatcacttgccaggcgagtcaggacattgg cacctctttaaattggtat-caacagagaccaggagagcccctacagtcctgatctatgatgcatccaatttgca-aacaggggtcccgtc aaggttcagtggaagtggatctgggaca-cattttactttcaccatcagcagcctg-cagtctgaagatattgcaacatatcactgtcaacag tatcataatgtcctgta-cagtttttggccaggggaccaaactggagatcaagc (SEQ ID NO 48). In one embodiment, coding sequence of a light chain V gene of this invention, encoding anti-AChR Fabs from AMC-M2, has nucleotide sequence that corresponds to gagctcgtgatgac-ccagtctccatcctccctgtctgcatct-gtaggagacagagtcaccatcacttgccgggcaagtcagaaccttag aaatgatt-taggactctggtatcagcagaaaccagggaaagcccctaacctcctgatctatggt-gcatccagtttacaaagtggggtcc catcaaggttcagcggcggtgggtctg-gcacagatttcactctcaccatcag-cagcctgcagcctgaagattttgcaacttattactgtct acaggattacaattac-ccgtggacgttcggccaagggaccaaggtggagatcaaac (SEQ ID NO 49). In one embodiment, coding sequence of a light chain V gene of this invention, encoding anti-AChR Fabs from AMC-M2, has nucleotide sequence that corresponds to gagctcgtgat-gacccagtctccatcctccctgtct-gcgtctattgggaacagagtcaccatcacttgccaggcgagtcaggacattgg cacctctttaaattggtatcacca-gaaaccagggaaagcccctaacctcct-gatctacggtgcatccagtttgcaaagtggggtcccctc aaggttcaatggcagtg-gatctggaacagatttcactctcaccatcaccagtctgcaacctgaggattttgcag-cttactactgtcaacag agtttcagtgtccctacnactttggc-caggggaccaagctggagatcacgc (SEQ ID NO 50).

In one embodiment, coding sequence of a heavy chain V gene of this invention, encoding anti-AChR Fabs from AMC-M6, has nucleotide sequence that corresponds to ctc-gagtcggggggaggcctggtcaagcct-gagggtcccctaagactctcctgtattgcctctggattcacctttaatacctacaatatg aattgggtccgtcagcctccagg-gaaggcctggaatgggtcgcttccat-aacagcgactagcagtcacacagagtacggaagctcc gttgcgggacgcttcac-catctccagagacaacaccaagaagtctctttatctagacatgacccgtctgagag-ccgaagacacggcac tttattttttgtgttcgagagtggggaag-tagattcatcactacgtttcggggcct-tcctcacttcgacctctggggccagggagccctggt atcgtctcgtca (SEQ ID NO 34). In one embodiment, coding sequence of a heavy chain V gene of this invention, encoding anti-AChR Fabs from AMC-M6, has nucleotide sequence that corresponds to ctcgagtcggggggaggcctggtcaagc-ctgagggtccctaagactctcctgtat-tgcctctggattcacctttaatacctacaatatg aattgggtccgtcagcctccagg-gaaggggactggaatgggtcgcttcaataacagcgactagcagtcacacagagta-cggaggctc cgttgcgggacgcttcaccatctcca-gagacaacgccaagaagtctctt-tatctagacatgacccgtctgagagccgaagacacggca ctttattttttgtgttc-gagagtggggagtagattcatcactacgtttcggggccttcctcacttcgacctct-ggggccagggagccctggt catcgtctcgtca (SEQ ID NO 35). In one embodiment, coding sequence of a heavy chain V gene of this invention, encoding anti-AChR Fabs from AMC-M6, has nucleotide sequence that corresponds to ctcgagtctgggggag-gcctggtcaagcctgagggtccctaaggctctcctgtcttgcctctggattca cctttaatacctacaatatgaat-tgggtccgtcagcctccagggaagg-gactggaatgggtcgcttcaataacagcgactagcagtcac acagagtacgag-gctccgttgcgggacgcttcaccatctccagagacaacaccaagaagtctctttat-ctagacatgacccgcctga gagccgaagacacggcactt-tattttttgtgttcgagaatggggaagca-gattcatcacaacatttcggggccttcctcacttcgacctctg ggggccagggagc-cctggtcatcgtctcgtca (SEQ ID NO 36). In one embodiment, coding sequence of a heavy chain V gene of this invention, encoding anti-AChR Fabs from AMC-M6, has nucleotide sequence that corresponds to ctcgagtctgggggaggcctggtcaagc-ctgacgggtcccgaaggctctcctgtgt-tgcctctggattcaccttaacacctacaatatg aattgggtccgtcagcctccagg-gaagggactggaatgggtcgcttcaataacgtcgactagcagtcatacagagtac-ggaggctcc gttgcgggccgcttcaccatctcca-gagacaacaccaagaagtctctt-tatctggacatgacccgtctgagagccgaggacacggca ctttattttttgtgttc-gagagtggggaagtagattcatcactacgtttcggggccttcctcatttcgacctct-ggggccagggagccctggt catcgtctcgtca (SEQ ID NO 37). In one embodiment, coding sequence of a heavy chain V gene of this invention, encoding anti-AChR Fabs from AMC-M6, has nucleotide sequence that corresponds to ctcgagtctgggggag-gcctggtcaagcctgaggggtccctaagactctcctgtattgcctctggattca cttttaatacctacaatatgaat-tgggtccgtcaaactccagggaagg-gactggagtgggtcgcatcaataagtacgactagcagtcac acagagtacaca-gactccgttgcggggcgcttcaccatctccagagacaacaccaagaagtctcttta-tctagacatgaccagcctga gagccgaagacacggcacttttattat-tgtgtgcgagaatggggcagtagat-tcatcacttcgtttcggggccttcctcactttgacctctg gggccagggagccctg-gtcatcgtctcctca (SEQ ID NO 38). In one embodiment, coding sequence of a heavy chain V gene of this invention, encoding anti-AChR Fabs from AMC-M6, has nucleotide sequence that corresponds to ctcgagtcgggggaggcctggtcaagc-ctgaggggtccctaagactctcctgtgt-tgcctctggattcacgtttaacacctacaacat gaattgggtccgtcagcctccagg-gaagggcctggagtgggtcgcctcaataacaacgactagcagtcatacagagta-tggaggctc tgttgcggagcggttcagcatctcca-gagacaacaccaagaagtcctg-tatctagacatgacccgtctgagagccgaagacacggc acttattttttgtgttc-gagaatacgaagtagatttatcactccatttcggggccttcctcactttgacctctg-gggcctgggagcccgggt catcgtctcgtca (SEQ ID NO 39). In one embodiment, coding sequence of a heavy chain V gene of this invention, encoding anti-AChR Fabs from AMC-M6, has nucleotide sequence that corresponds to ctcgagtcgggcccag-gactgctaaagccttcacagaccctgtccctcacctgctctgtctctggtgcct ccctcagtcgtggtgcatacttctg-gacttggatccggcagccggccgg-gaagggactggaatggattggtcgtgtctataccattgag aacaccgtctacaac-ccctccctcaggagtcgagtcaccatgtctgtcgacacgtccaagaacttattctcc-ctggacctgcgctctgtc acctccgcagacacggccgtctattat-tgtgcgagagggaggggggaagttcgaac-tacttgacttctggggccagggaatcccggtc accgtctcgtca (SEQ ID NO 40). In one embodiment, coding sequence of a heavy chain V gene of this invention, encoding anti-AChR Fabs from AMC-M6, has nucleotide sequence that corresponds to ctc-gagtctgggggaggcttggtacagc-cagggcggtccctgagactctcctgtgcagcctctgggattcaccttagcacctatg-ccct ggcctgggtccgccaggctccagg-gaaggggctggagtgggtctcagttat-caataatagtggtggcagcacatattatgcagtctcc gtgagcggccggttcgc-catctccagagataattccaagaacacgctgtatctagagatgcgcagcctgaga-gccgaggacacggc cgtctatttctgtgccaaagggaag-gacggactgattatactacccggcgc-tatggacgtctggggccaagggaccgcggtcaccgt gtcctca (SEQ ID NO 41).

In one embodiment, coding sequence of a light chain V gene of this invention, encoding anti-AChR Fabs from AMC-M6, has nucleotide sequence that corresponds to gagctcgtgat-gacccagtctccatcctccgtgtct-gcgtctcctggtgacagagtcactatttcttgccgggcaagtgagaccgttaata catatctcaactggtaccaacaaaaa-cagggagaggcccctaaagtcctaatctactctgcatccactttgcaaagagacgtcccgtcg aggttcagtggcagtggatctgggacagatttcactctcaccatcaccaatgtacagcctgacgattttgcaacttactattgtcaacaga gttatttaaccccctctcactttcggcggcgggaccagggtcgatctccga (SEQ ID NO 51). In one embodiment, coding sequence of a light chain V gene of this invention, encoding anti-AChR Fabs from AMC-M6, has nucleotide sequence that corresponds to gagctcgtgatgaccagtctccatcctccctgtct-
gcgtctcctggtgacagggtcactatttcttgccgggcaagtgagaccgttaata catatctcaactggtaccaacaaaaa-
caggggggaggcccctaaagtcctgatc-
tactctgcatccactttgcaaagagacgtcccgtcg aggttcagtggcagtggatctgggacagatttcactctcaccatcaccaatctgcagcctgaagattttgcaacttactattgtcaacaga gttatttaaccccctctcactttcggcggcgggaccaaggtggatctcaaa (SEQ ID NO 52). In one embodiment, coding sequence of a light chain V gene of this invention, encoding anti-AChR Fabs from AMC-M6, has nucleotide sequence that corresponds to gagctcgtgatgaccagtctccatccaccctgtct-
gcgtctcttggagacagagtcactatttcttgccgggcaagtgagaccattaag acatatttaaattggtaccaacaaaaa-
caaggagaggcccctaaggtcct-
gatctcttcagcatccactttgcaaagagacgtctcatcg aggttcagtggcagtgggtctgggacagatttcactctcaccatcaacaatctgcagcctgaagatttgcaacttactactgtcagcaga gttacactaccccctctcactttggcg-gagggaccaaggtcgatctcaaa (SEQ ID NO 53). In one embodiment, coding sequence of a light chain V gene of this invention, encoding anti-AChR Fabs from AMC-M6, has nucleotide sequence that corresponds to gagctcgtgatgaccagtctccatctccctgtct-
gcgtctcttggagacagagtcactatttcttgccgggcaagtcagaccattgata catatttaaattggtaccaaccaaaac-
caggagaggcccctaaggtcctgatc-
cattctgcatccactttgccaagagaggtcccatcga ggttcagtggcagtggatctgggacagatttcactctcaccatcaccaatctgcagcctgaagattttgcaacttactactgtcaacagag ttttacaaccccctctcactttcggcg-gagggaccaaggtggatctcaaa (SEQ ID NO 54). In one embodiment, coding sequence of a light chain V gene of this invention, encoding anti-AChR Fabs from AMC-M6, has nucleotide sequence that corresponds to gagctcgtgatgac-ccagtctccatccaccctgtct-
gcgtctcttggagacagagtcactatttcttgccgggcaagtgagaccattaag acatatttaaattggtaccaacaaaaa-
caaggagaggcccctaaggtcct-
gatctctgcagcatccactttgcaaagagacgtctcatcg aggttcagtg-gcagtgggtctgggacagatttcactctcaccatcaacaatctgcagcctgaagattttgcaacttactactgtcagcaga gttacactaccccctctcactttcggcg-gagggaccaaggtcgatctcaaa (SEQ ID NO 55). In one embodiment, coding sequence of a light chain V gene of this invention, encoding anti-AChR Fabs from AMC-M6, has nucleotide sequence that corresponds to gagctcgtgatgaccagtctccatcctccctgtct-
gcgtctcttggagacagagtcactatttcttgccgggcaagtcagaccatcaatt caaatttaaattggtatcaaccaaaac-
caggagaggcccctaaggtcct-
gatctctgcagcatccagtttgcaaagagaagtcccatcg aggttcagtg-gcagtggatctgggacagatttcactctcaccatcagcaatctgcagcctgaagatt-ttgcaacttactactgtcagcaga gttacactaccccctctcactttcggcg-gtgggaccaaggtggatctcaaa (SEQ ID NO 56). In one embodiment, coding sequence of a light chain V gene of this invention, encoding anti-AChR Fabs from AMC-M6, has nucleotide sequence that corresponds to gagctcgtgatgaccagtctccatcctccctgtctgcatct-
gtaggagacaaagtcaccatcacttgccgggcaagtcagagcattag caactatt-taaattggtatcagcagaaaccagggaaagccccctaaactcctgatctctgctgca-tccagtttgcaaagtgtggtccatca aggtcagtggcagtggatctggcacg-gatttcactctcaccatcagcggtctacaacctgaagatttttgcaacctactactgtcagcag agttacaatacccctaa-cactttcggccccgggaccaaagtggatatcaga (SEQ ID NO 57). In one embodiment, coding sequence of a light chain V gene of this invention, encoding anti-AChR Fabs from AMC-M6, has nucleotide sequence that corresponds to gagctcgtgatgac-ccagtctccagactccttggctgt-
gtctctgggcgagagggccaccatcaactgcaagtccagccagaatcttt ata-cagcgtcaacaataaaaactacatagcttggttccagcagaaaccaggacagcc-gcctaagttgctcatttactgggcatctatccg ggaatccggggtccctgaccgat-tcagtggcagcggatctgagaca-
gatttcactctcaccatcagcagcctgcaggctgaagatgtg gcagtttattattgt-cagcaatattctggttttcgtggacattcggccaagggaccaaggtggaaatcaaa (SEQ ID NO 58).

On the basis of these results, it is suggested that the initial immunization is by the fetus, generating a restricted group of mutated 'progenitor' memory cells, possibly in lymph nodes draining the uterus. Consequently, circulating antibodies are produced against fetal AChR; they attack rare myoid cells in the thymus that express this isoform, releasing antibody: AChR complexes that provoke local GC formation very efficiently. The progenitor memory cells are attracted by the complexes trapped in these GC, and undergo further rounds of mutation and selection, culminating in the expanded populations of clonally related B cells and plasma cells that we have detected (see Table 3,which is in FIG. 13 and FIG. 4). Several autoimmune diseases show both a strong female bias and onset in early adulthood (e.g SLE, thyroid disease, multiple sclerosis and EOMG); there is evidence for the importance of hormonal influences in the autoimmune response, as well as potential X chromosome contributions in these diseases. Persisting fetal—maternal microchimerism has also been invoked because of the recent findings of fetal or maternal RNA in scleroderma lesions. There are already well known examples of alloimmunization of mothers, for example, by fetal erythrocytes or platelets. While it might be informative to look for allotypic variations in the AChR γ subunit, the AChR is remarkably autoimmunogenic, even without adjuvant. Although the majority of EOMG female patients present before pregnancy, our results suggest that autoimmunization by the fetus is another possible route to maternal MG, perhaps enhanced by presentation by semi-allogeneic (fetal) cells.

Figure 10E:
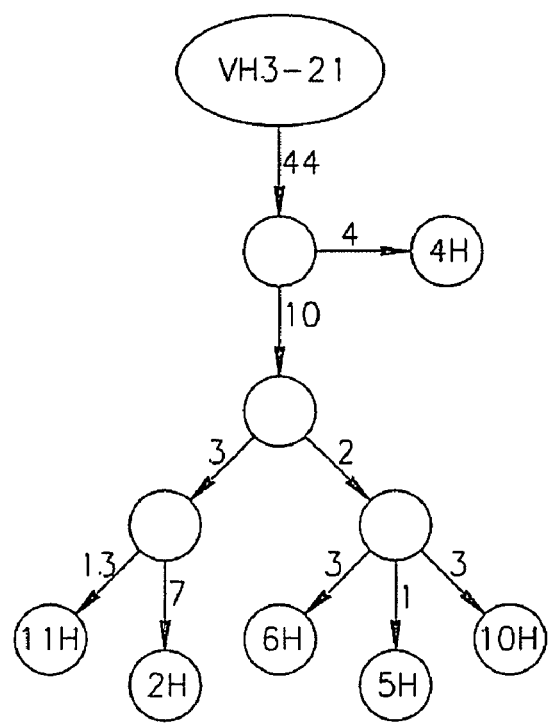
FIG. 10 shows evolution of VH and VK clones from AMC-6.
Figure 10F:
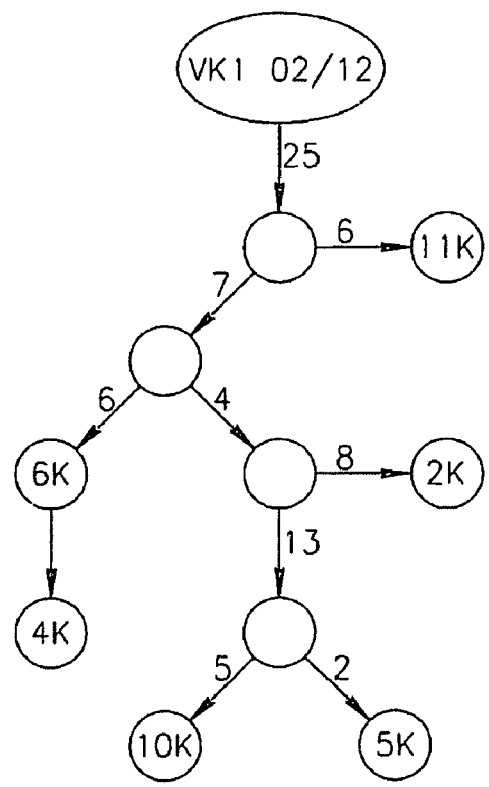

Evolution of DNA sequences and encoded amino acid sequences thereof, in human immunoglobulin AMC-M6 VH3-21 (heavy chain) and human VK1 02/12 (light chain) clones are presented in FIG. 10 (A-D). In one embodiment, a VH3-21 immunoglobulin heavy chain clone of this invention has a nucleotide sequence, which corresponds to gggctgagag-caaccttcagtagctatagcaaccgc-
caggctggggagtcatccattagtagtagtagttacatatactacgcagactc agt-gaagggccgaaccgccaactcactgctgcaaaacagcgaggctgtgtac (SEQ ID NO 59). In one embodiment, a VH3-21 immunoglobulin heavy chain clone (AMC-M6 10H) of this invention has a nucleotide sequence, which corresponds to gagctaagaattac-ctttaatacctacaataatcgtcagc-
ctggagaagcttccataacagcgactagccacacagagtacggaagctc cgt-tgcgggacgcaccaccaagtctcttctagacacccgtgaagcactttt (SEQ ID NO 60). In one embodiment, a VH3-21 immunoglobulin heavy chain clone (AMC-M6 5H) of this invention has a nucleotide sequence, which corresponds to gagctaagaattac-ctttaatacctacaataatcgtcagc-
ctggagaagcttcaataacagcgactagccacacagagtacggaggctc cgt-tgcgggacgcaccgccaagtctcttctagacacccgtgaagcactttt (SEQ ID NO 61). In one embodiment, a VH3-21 immunoglobulin heavy chain clone (AMC-M6 6H) of this invention has a nucleotide sequence, which corresponds to gagctaaggcttac-ctttaatacctacaataatcgtcagc-
ctggagaagcttcaataacagcgactagccacacagagtacggaggctc cgt-tgcgggacgcaccaccaagtctcttctagacacccgcgaagcactttt (SEQ ID NO 62). In one embodiment, a VH3-21 immunoglobulin heavy chain clone (AMC-M6 2H) of this invention has a nucleotide sequence, which corresponds to gaccgaagggttac-ctttaacacctacaataatcgtcagc-ctggagaagcttcaataacgtcgactagccatacagagtacggaggct ccgt-tgcgggccgcaccaccaagtctcttctggacacccgtgaggcacttttt (SEQ ID NO 63). In one embodiment, a VH3-21 immunoglobulin heavy chain clone (AMC-M6 4H) of this invention has a nucleotide sequence, which corresponds to gagctaagaattacttt-taatacctacaataatcgtcaaactg-gagaggcatcaataagtacgactagccacacagagtacacagactc cgt-tgcggggcgcaccaccaagtctcttctagacaccagcgaagcactttat (SEQ ID NO 64). In one embodiment, a VH3-21 immunoglobulin heavy chain clone (AMC-M6 11H) of this invention has a nucleotide sequence, which corresponds to gagctaagagt-tacgtttaacacctacaacaatcgt-cagcctggcgaggcctcaataacaacgactagccatacagagtatggaggct ctgttgcggagcggagcaccaagtccctgctagacacccgtgaagcacttttt (SEQ ID NO 65).

In one embodiment, a VK1 02/12 immunoglobulin light chain clone of this invention has a nucleotide sequence, which corresponds to tccctggcagtaggaagaaccatcact-cagagcattagcagctatttaaattat-cagcagccagggaaaaagctcctgtatgctagtca aagtgggccatcaggaag-cagtctgcaagaataccaatacagt (SEQ ID NO 66). In one embodiment, a VK1 02/12 immunoglobulin light chain clone (AMC-M6 10K) of this invention has a nucleotide sequence, which corresponds to tccgtggcgcctggtagaactatttct-gagaccgttaatacatatctcaactac-caacaacagggagagaaagtcctatactctactcaa agagacccgtcgggaac-caatgtacaggactatcaatattta (SEQ ID NO 67). In one embodiment, a VK1 02/12 immunoglobulin light chain clone (AMC-M6 5K) of this invention has a nucleotide sequence, which corresponds to tccctggcgcctggtaggactatttct-gagaccgttaatacatatctcaactac-caacaacaggggggagaaagtcctgtactctactcaa agagacccgtcgggaac-caatctgcaggaatatcaatattta (SEQ ID NO 68). In one embodiment, a VK1 02/12 immunoglobulin light chain clone (AMC-M6 6K) of this invention has a nucleotide sequence, which corresponds to accctggcgcttggaagaactatttct-gagaccattaagacatatttaaattac-caacaacaaggagagaaggtcctgtcttcaactcaa agagactcatcggggaa-caatctgcaggaataccagtacact (SEQ ID NO 69). In one embodiment, a VK1 02/12 immunoglobulin light chain clone (AMC-M6 2K) of this invention has a nucleotide sequence, which corresponds to tccctggcgcttggaagaactatttct-cagaccattgatacatatttaaattac-caaccaccaggagagaaggtcctgcattctactccaa gagagccatcgggaac-caatctgcaggaataccaatttaca (SEQ ID NO 70). In one embodiment, a VK1 02/12 immunoglobulin light chain clone (AMC-M6 4K) of this invention has a nucleotide sequence, which corresponds to accctggcgcttggaagaactatttct-gagaccattaagacatatttaaattac-caacaacaaggagagaaggtcctgtctgcaactcaa agagactcatcggggaa-caatctgcaggaataccagtacact (SEQ ID NO 71). In one embodiment, a VK1 02/12 immunoglobulin light chain clone (AMC-M6 11K) of this invention has a nucleotide sequence, which corresponds to tccctggcgcttggaagaactatttct-cagaccatcaattcaaatttaaattat-caaccaccaggagagaaggtcctgtctgcaagtcaaa gagaaccatcgggaag-caatctgcaggaataccagtacact (SEQ ID NO 72).

In one embodiment, a VH3-21 immunoglobulin heavy chain clone of this invention encodes an amino acid sequence, which corresponds to GLRATFSSYSNRQAGESSISSSSY-IYYADSVKGRTANSLLQNSEAVY (SEQ ID NO 73). In one embodiment, a VH3-21 immunoglobulin heavy chain clone (AMC-M6 10H) of this invention encodes an amino acid sequence, which corresponds to ELRITFNTYNNRQP-GEASITATSHTEYGSSVAGRTTKSLLDTREALF (SEQ ID NO 74). In one embodiment, a VH3-21 immunoglobulin heavy chain clone (AMC-M6 5H) of this invention encodes an amino acid sequence, which corresponds to ELRITFN-TYNNRQPGEASITATSHTEYGGSVAGR-TAKSLLDTREALF (SEQ ID NO 75). In one embodiment, a VH3-21 immunoglobulin heavy chain clone (AMC-M6 6H) of this invention encodes an amino acid sequence, which corresponds to ELRLTFNTYNNRQPGEASITATSH-TEYGGSVAGRTTKSLLDTREALF (SEQ ID NO 76). In one embodiment, a VH3-21 immunoglobulin heavy chain clone (AMC-M6 2H) of this invention encodes an amino acid sequence, which corresponds to DRRVTFNTYNNRQP-GEASITSTSHTEYGGSVAGRTTKSLLDTREALF (SEQ ID NO 77). In one embodiment, a VH3-21 immunoglobulin heavy chain clone (AMC-M6 4H) of this invention encodes an amino acid sequence, which corresponds to ELRITFN-TYNNRQTGEASISTTSHTEYTDSVAGRT-TKSLLDTSEALY (SEQ ID NO 78). In one embodiment, a VH3-21 immunoglobulin heavy chain clone (AMC-M6 11H) of this invention encodes an amino acid sequence, which corresponds to ELRVTFNTYNNRQPGEASITTTSH-TEYGGSVAERSTKSLLDTSEALF (SEQ ID NO 79).

In one embodiment, a VK1 02/12 immunoglobulin light chain clone of this invention encodes an amino acid sequence, which corresponds to SLAVGRTITQSISSYL-NYQQPGKKLLYASQSGPSGSSLQEYQYS (SEQ ID NO 80). In one embodiment, a VK1 02/12 immunoglobulin light chain clone (AMC-M6 10K) of this invention encodes an amino acid sequence, which corresponds to SVAPGR-TISETVNTYLNYQQQGEKVLYSTQRDPS-GTNVQDYQYL (SEQ ID NO 81). In one embodiment, a VK1 02/12 immunoglobulin light chain clone (AMC-M6 5K) of this invention encodes an amino acid sequence, which corresponds to SLAPGRTISETVNTYLNYQQQGEKV-LYSTQRDPSGTNLQEYQYL (SEQ ID NO 82). In one embodiment, a VK1 02/12 immunoglobulin light chain clone (AMC-M6 6K) of this invention encodes an amino acid sequence, which corresponds to TLALGRTISETIKTYL-NYQQQGEKVLSSTQRDSSGNNLQEYQYT (SEQ ID NO 83). In one embodiment, a VK1 02/12 immunoglobulin light chain clone (AMC-M6 2K) of this invention encodes an amino acid sequence, which corresponds to SLALGR-TISQTIDTYLNYQPPGEKVLHSTPREPSGTNLQEYQFT (SEQ ID NO 84). In one embodiment, a VK1 02/12 immunoglobulin light chain clone (AMC-M6 4K) of this invention encodes an amino acid sequence, which corresponds to TLA-LGRTISETIKTYLNYQQQGEKVL-SATQRDSSGNNLQEYQYT (SEQ ID NO 85). In one embodiment, a VK1 02/12 immunoglobulin light chain clone (AMC-M6 11K) of this invention encodes an amino acid sequence, which corresponds to SLALGRTISQTIN-SNLNYQPPGEKVLSASQREPSGSNLQEYQYT (SEQ ID NO 86).

In another embodiment, the invention provides a method of inducing immune tolerance to fetal AchR in a recipient at risk of developing Myasthenia Gravis comprising the step of exposing the recipient to tolerogenic amount of fetal AChR, thereby inducing immune tolerance in a recipient at risk of developing Myasthenia Gravis.

In another embodiment, the invention provides a method of inducing immune tolerance to fetal AchR in a recipient at risk of developing arthrogryposis multiplex congenita comprising the step of exposing the recipient to tolerogenic amount of fetal AChR, thereby inducing immune tolerance in a recipient at risk of developing arthrogryposis multiplex congenita.

The recipient at risk of developing arthrogryposis multiplex congenita is a newborn to a pregnant mother, who has symptoms of Myasthenia Gravis, or who has a history family of either Myasthenia Gravis or arthrogryposis multiplex congenita.

The recipient at risk of developing Myasthenia Gravis is a mother who has a history family of Myasthenia Gravis and in another embodiment, who has a history family of Myasthenia Gravis in pregnancy.

In another embodiment, the invention provides a method of preventing Myasthenia Gravis in a recipient at risk of developing Myasthenia Gravis comprising the step of exposing the recipient to tolerogenic amount of fetal AChR, thereby inducing immune tolerance in a recipient at risk of developing Myasthenia Gravis.

In another embodiment, the invention provides a method of preventing arthrogryposis multiplex congenita in newborn of mothers with Myasthenia Gravis comprising the step of administering a tolerating amount of fetal AChR to mothers with Myasthenia Gravis or that are at risk of developing Myasthenia Gravis.

In one embodiment of the invention, inducing tolerance may be referred to unresponsiveness to an antigen without inducing a prolonged generalized immune deficiency. Tolerance represents an induced depression in the response to an antigen.

As used herein, "antigen" refers to a substance, which elicits an immune response. The antigens of the invention to which tolerance is induced may or may not be exogenously derived relative to the host. For example, the method of the invention may be used to induce tolerance to an "autoantigen". An autoantigen is a normal constituent of the body that reacts with an autoantibody.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

EXAMPLES

Experimental Procedures

Generation of Anti-AChR Fab and scFv Fragments

Figure 1:
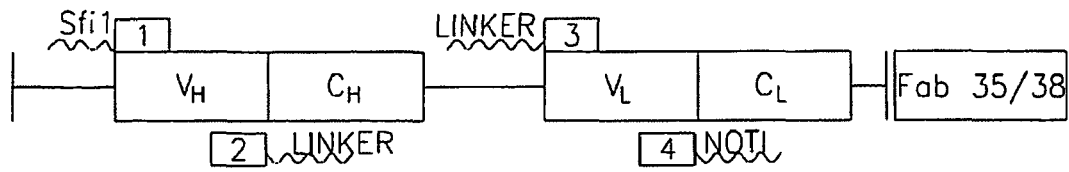
FIG. 1 is a schematic presentation of the synthesis of scFv fragments based on the recombinant Fab fragments Fab35 and Fab38 using overlap extension PCR.
Figure 1:
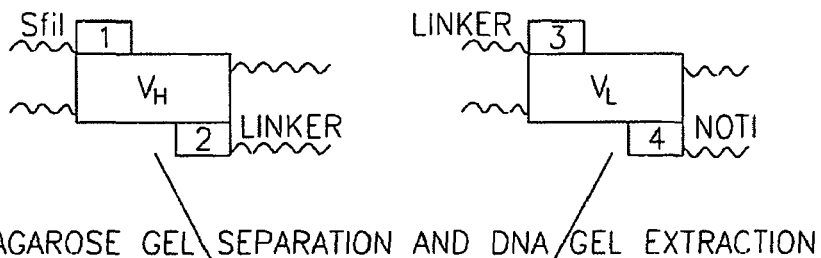
Figure 1:
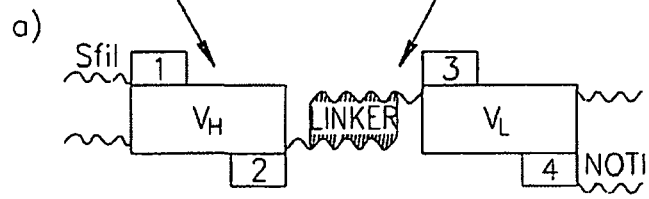
Figure 1:
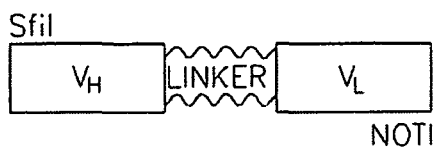

The cloning and expression of the high-affinity rat 195-scFv fragment derived from the anti-AChR rat antibody mAb195 with specificity to the α67-76 sequence (main immunogenic region, MIR) has been described previously. The generation of the recombinant human Fab fragments Fab35 and Fab38 using a combinatorial cDNA thymus library of a patient with thymic lymphoid hyperplasia and production autoantibodies specific for the anti-AChR γ-subunit has been described as well. ScFv fragments were produced from Fab35 and Fab38 by overlap extension as shown in FIG. 1. For each Fab, two recombinant scFv fragments were generated: one in a VH-VL, the other in a VL-VH orientation. The respectve primers were as follows:

Primers for scFv from Fab35/38 in Orientation $V_H$-$V_L$
scFv/Fab35 $V_H$5' SfiI:

5'-AGTCTAAGGTTCGGCCCAGCCGGCCTCGGGG   (SEQ ID. No. 1)
GGCGACTTGGTCCAGCCGGGGGGG-3' scFv/Fab38 $V_H$5' Sfi I:

5'-AGTCTAACGTTCGGCCCAGCCGGCCTCGGGG   (SEQ ID. No. 2)
GAGGCGTGGTCCAGCCGGGGGGG-3' scFv/Fab35/38 $V_H$3' Linker:

5'-GCCACCCGACCCACCACCGCCCGAGCCACCGC   (SEQ ID. No. 3)
CACCTGGAGAGACGGTGACCGTTGTCCCTTGGC
C-3' scFv/Fab35/38 $V_L$5' Linker:

5'-GGCTCGGGCGGTGGTGGGTCGGGTGGCGGCGG   (SEQ ID. No. 4)
ATCAGTGATGACCCAGTCTCCA-3' scFv/Fab35 $V_L$3' Not I:

5'-TGCTGCTGCGGCCGCTTTGATCTCCAGCTTGG   (SEQ ID. No. 5)
TCCC-3' scFv/Fab38 $V_L$3' Not I:

5'-TGCTGCTGCGGCCGCCGTGATCTCCAGCTTGG   (SEQ ID. No. 6)
TCCC-3'

Primers for scFv from Fab35/38 in Orientation $V_L$-$V_H$
scFv/Fab35/38 $V_L$5' Sfi I:

5'-ATGGCTCAGGGTTCGGCCCAGCCGGCCGTGAT   (SEQ ID No. 7)
GACCCAGTCTCCA-3' scFv/Fab35 $V_L$3' Linker:

5'-GCCACCCGACCCACCACCGCCCGAGCCACCGC   (SEQ ID. No. 8)
CACCTTTGATCTCCAGCTTGGTCCC-3' scFv/Fab38 $V_L$3' Linker:

5'-GCCACCCGACCCACCACCGCCCGAGCCACCGC   (SEQ ID. No. 9)
CACCCGTGATCTCCAGCTTGGTCCC-3' scFv/Fab35 $V_H$5' Linker:

5'-GGCTCGGGCGGTGGTGGGTCGGGTGGCGGCGG   (SEQ ID. No. 10)
ATCATCGGGGGCGACTTGGTCCAGCCGGGGG
GG-3' scFv/Fab38 $V_H$5' Linker:

5'-GGCTCGGGCGGTGGTGGGTCGGGTGGCGGCG (SEQ ID. No. 11)
GATCATCGGGGGAGGCGTGGTCCAGCCGG
GGGGG-3' scFv/Fab35/38 $V_H$3' Not I:

5'-TGCTGCTGCGGCCGCTGGAGAGACGGTGACG (SEQ ID. No. 12)
GTTGTCCCTTGGCC-3'

Production and Purification of the Immuntoxines (IT)

The protocol for the production and purification of recombinant ITs was published recently. In brief E. coli strain BL21DE3 lys (Stratagene, Heidelberg, Germany) were transformed with the corresponding plasmids. A preculture of 10 ml LB medium/50 µg/µl Kanamycin was inoculated and incubated for 6-8 hours at 37° C. 5 ml of this preculture were added to 500 ml Terrific Broth/0,5 mM ZnCl/50 µg/µl Kanamycin and shaken overnight at 26° C. After 14-16 hours of incubation, the 500 ml culture was divided on 5 l Terrific Broth/0.5 mM ZnCl/50 µg/µl Kanamycin (in 20 1 1-flasks each containing 250 ml medium) and incubated for further 3-5 hours at 26° C. After adding Sorbitol, NaCl and Betain to a final concentration of 0.5M, 4% and 110 mM respectively, cultures were grown for 30 min. and protein production was induced by IPTG (final concentration 1-2 mM/l) and overnight shaking.

On the next day bacteria were harvested by centrifugation (3700 g, 4° C.), pellets were washed in 1× wash buffer (75 mM Tris pH8.8, 4% NaCl and 10% glycerol) resuspended again in 1× wash buffer and frozen in liquid nitrogen. Bacteria were lysed in 1× lysis buffer (75mM Tris/HCl pH 8.8, 300 mM NaCl, 10% glycerol, 5 mM DTT, PMSF/EDTA, 5 mM EDTA), sonified and centrifugated (25000 g, 4° C., 60 min.). The supernatant was filtered, desalted by FPLC and desalting column (Amersham Biosciences, Heidelberg, Germany) (flow rate 6 ml/min). The pooled protein fractions were purified and eluted by a Nickel-NTA-Agarose column (Quiagen, Hilden, Germany) with 1× elution buffer (75 mM Tris/HCl pH 8.8, 10% glycerol, 1 M NaCl, 0.5 M Imidazol) and a flow rate of 6 ml/min.

Subsequently aliquots of the corresponding fractions were loaded on a 6% SDS acrylamidgel and prtoein was blotted onto nitrocellulose membrane as described recently.

Colorimetric XTT Cytotoxicity Assay and RMS Cell Lines

The assay is based on the metabolization of the yellow tetrazolium salt XTT (conzentration: 1.49 mM, Roche, Molecular Biochemicals, Mannheim, Germany) to the orange and water soluble chromogen formazan. The concentration of formazan is measured at 450 nm und 650 nm by a 96 well plate elisa detector (MWG Biotech, Ebersberg, Germany). Supernatants were checked for chromogen development 96 h after the beginning of IT application to cell cultures grown at subconfluent density.

As IT targets and controls, the following cell lines were tested: Embryonal RMS cells (TE761), alveolar RMS (RD); muscle-type AChR-negative controls: IMR32 (neuroblastoma); U937 (hematologic precursor cells line); A431 (squamous cell carcinoma cell line).

Generation and Treatment of RMS in an In-Vivo Nude Mouse Model

Subcutaneous injection of $5\times10^6$ TE671 cells suspended in DMEM serum-free culture medium on day 1 served to generation RMS in nude mice (n=10). Starting on day 2 up to day 10, mice received either 10 mg scFv3 5-ETA (n=6) or saline (n=4) twice daily intraperioneally as described for othet toxins previously. Tumour size was checked manually on day 5 and then every third day up to day 20, when mice were killed and autopsied for detection of metastases. Tumour explants were measured for size and subdivided for a) shock freezing; b) embedding in paraffin; c) FACS analysis using scFv35-ETA (and a polyclonal antiserum, Santa Cruz).

Immunhistochemistry and Detection of AChR α and γ Subunit mRNA by Semiquantitative Multiplex PCR Immunhistochemical detection of the fetal AChR on frozen and paraffin-embedded sections was achieved by a polyclonal goat antiserum specific for the AchR γ-subunit (Santa Cruz, Santa Cruz, USA) as described previously.

For simultaneous amplification of the α and γ subunit mRNA of the AchR and the to determination of the γ/α ratio, a semiqunatitative multiplex RT-PCR was performed as reported previously.

Clinical Material

Patient material was obtained with informed consent and Ethical Committee approval. Sera from MG patients were collected in Professor John Newsom-Davis' clinic, before thymectomy or immunosuppression, and stored at −20° C. Antibodies to AChR were measured as previously described (Vincent et al 1995; Riemersma et al 1997). AMC-M2 and AMC-M6, described in (Riemersma et al 1997; Jacobson et al 1999), had had four and two babies, respectively, with severe AMC (fatal in all but one), but the diagnosis of maternal MG was made only after the birth of the AMC babies. After therapeutic thymectomy and immunosuppressive therapies for their MG, and plasma exchange during pregnancy, both mothers have subsequently had successful pregnancies with minimally affected babies (unpublished observations). Thymus cell suspensions were prepared and cryopreserved as in (Willcox, Newsom-Davis and Calder 1983). From both patients, these cells spontaneously produced high levels of anti-AChR antibodies in culture that were reduced by pokeweed mitogen, typical of plasma cell behavior (Willcox, Newsom-Davis and Calder 1983); these antibodies showed a strong preference for fetal AChR, and also inhibited its ion channel function (not shown), as did serum antibodies from AMC-M2 (Riemersma et al 1997) and AMC-M6.

Measurement of Inhibition of AChR Function in TE671 Cell Line

AChR function was measured in TE671 cells that express only fetal AChR, as previously described in (Riemersma et al 1997). Carbachol-induced $^{22}Na^+$ flux was measured over 1 minute, and the internalized $^{22}Na^+$ was counted on a Packard Autogamma counter. The inhibitory effect of the sera was tested by incubating the cells with 25 µl of serum in 500 µl Hepes Locke buffer (ie. 1:20) for 30 minutes. The results are expressed as % inhibition, with 0% being the cpm in Hepes Locke buffer alone and 100% inhibition being the cpm in cells tested in the presence 1 µg/ml of the antagonist α-bungarotoxin (α-BuTx). Those sera producing more than 50% inhibition were then retested at higher dilutions and the results are presented as % inhibition/µl of serum.

Combinatorial Ig Gene Library Construction

The Fab library was made from cDNA after reverse-transcription from mRNA obtained from thymic cells (Farrar et al 1997). We used an anti-sense primer for an IgG1 CH1 sequence (almost identical to its IgG3 homolog (Kabat et al 1991)) to amplify VH chain cDNA by PCR in combination with a panel of sense oligonucleotide primers designed to include VH1-VH6 gene families: further panels amplified the Vκ or Vλ gene families, as described in (Farrar et al 1997). The PCR products were ligated into Immunozap H or L bacteriophage vectors (Stratagene). Subsequently, the heavy and light chain DNAs were ligated into Immunozap to yield combinatorial libraries, as detailed in (Farrar et al 1997) and (Chazenbaik et al 1993).

Screening the Library for AChR-Binding Fabs

Positive clones were identified essentially as in (Farrar et al 1997). Muscle extracts from denervated muscles were labeled with 2 nM $^{125}$I-α-BuTx (Amersham International, Amersham, UK; specific activity 2000 Ci/mmol) and used to screen the unamplified combinatorial library in XL1-Blue cells by filter-lift assays. Positive plaques were identified by autoradiography, cloned to homogeneity, and the heavy and light chain genes were sequenced in both directions by the dideoxy chain termination method (Sanger et al 1977). To obtain soluble Fabs, the XL1-Blue cells were induced with 1 mM isopropyl-thio-galacto-pyranoside (Sigma, St Louis, Mo.) overnight. The cells were then pelleted and freeze/thawed in 10 mM Tris buffer pH 8.0 containing protease inhibitors (see (Farrar et al 1997)). The suspension was sonicated and cleared by centrifugation, to leave a Fab-containing lysate.

Characterizing Fab Reactivity with AChR

The lysates were used without further purification. They were incubated with AChR (either from muscle extracts, from TE671 cells or from a transfected subline that expresses predominantly adult AChR (Beeson et al 1996)), labeled with $^{125}$I-α-BuTx. After 2 hours at 20° C., carrier normal human serum was added plus a goat anti-human IgG (Lawrance Laboratories, Western Australia) which precipitated the Fab-AChR complexes efficiently. Competition with mAbs (Jacobson et al 1999) was measured by preincubating the $^{125}$I-α-BuTx-AChR with 50 µl of each Fab overnight at 4° C. and then adding excess (0.1 µl of ascites) of each mAb (see (Farrar et al 1997)). Sheep antibody to mouse IgG (which did not precipitate human Fabs) was then added to precipitate mAb-AChR complexes. All results were compared with precipitation in the presence of a control Fab that did not bind AChR, and expressed as the % inhibition by each Fab of the binding of the indicated mAb (see also (Whiting et al 1986)).

Bioinformatics

Sequences were compared with the human VBASE directory of immunoglobulin genes (Tomlinson et al 1997) using DNAPLOT (Müller, W. Institut für Genetik, Köln) to determine the best matching germline V-gene segments. Sequences with the same gene rearrangement and common CDR3s were judged to be clonally related. The numbers of somatic mutations over the VH and Vκ regions were determined, and ratios of replacement to silent mutations (R:S ratio) were calculated for framework (FWR) and complementarity-determining regions (CDR). Amino acid numbering and FWR and CDR positions were previously defined by Kabat et al (1991). Genealogical trees were constructed for sets of related genes by analysis of shared and unshared mutations using phylogenetic analysis using parsimony (PAUP) (Swofford 1993). Independent genes were also compared for the occurrence of convergent mutations.

Experimental Results

Example 1

An IT Targeting the Main Immunogenic Region (MIR) of the AChR α-Subunit Kills RMS Cells In Vitro In a first step we generated an ETA-containing IT based on a recombinant single chain Fv fragment that had been derived from the well characterized rat monoclonal antibody mAb195 against the main immunogenic region (MIR) of the human AChR α-subunit. This model IT (scFv-195-ETA) specifically bound to several RMS cell lines as revealed by FACS (not shown). Binding of scFv-195-ETA to TE671 RMS cells could be competed using unlabeled scFv-195 (not shown). In addition, scFv-195-ETA killed the RMS cell lines TE671, FLOH-1 and RD in a dose-dependant manner, while non-RMS epithelial, hematopoietic and neurogenic cell lines (A431; U937; IMR32, respectively) without muscular AChR expression were not killed (FIG. 2). These experiments were considered as "proof-of-principle" that specific targeting of the AChR by an IT can kill AChR-positive RMS cells. Since the α-subunit is shared by RMS cells and normal skeletal muscle, scFv195-ETA is not applicable in a therapeutic setting in humans.

Example 2

Synthesis of an IT Targeting the γ-Subunit of the Human Fetal AChR In Vitro

Since the fetal AChR, specified by the γ-subunit, is virtually absent in non-neoplastic innervated skeletal muscle but expressed in most RMS, we generated an ETA-based IT with specificity for the AChR γ-subunit. Synthesis started from two recombinant human Fab fragments (Fab35 and Fab38) that were derived from a combinatorial cDNA library derived from the thymus of a seropositive MG patient with high titers of anti-AChR γ-subunit antibodies. Although cloning of the two Fab fragment cDNAa into the ETA-vector resulted in constructs that were in frame as revealed by sequencing, they were inefficiently translated in transformed *E. coli* BL21DE3, resulting in several abnormal protein fragments of 70-80 kd instead of the expected 120 kd full-lenghth IT (not shown). Therefore, we used the Fab35 and Fab38 cDNAs to produced single-chain Fv (scFv) fragments by overlap extension PCR (FIG. 1). VH and VL fragments were linked by a 36 nucleotide (Glycin/Serine) spacer. ScFV fragments with a VH-VL and a VL-VH orientation were produced from both the Fab35 and Fab38, yielding 4 differentient scFvs.

Figure 3:
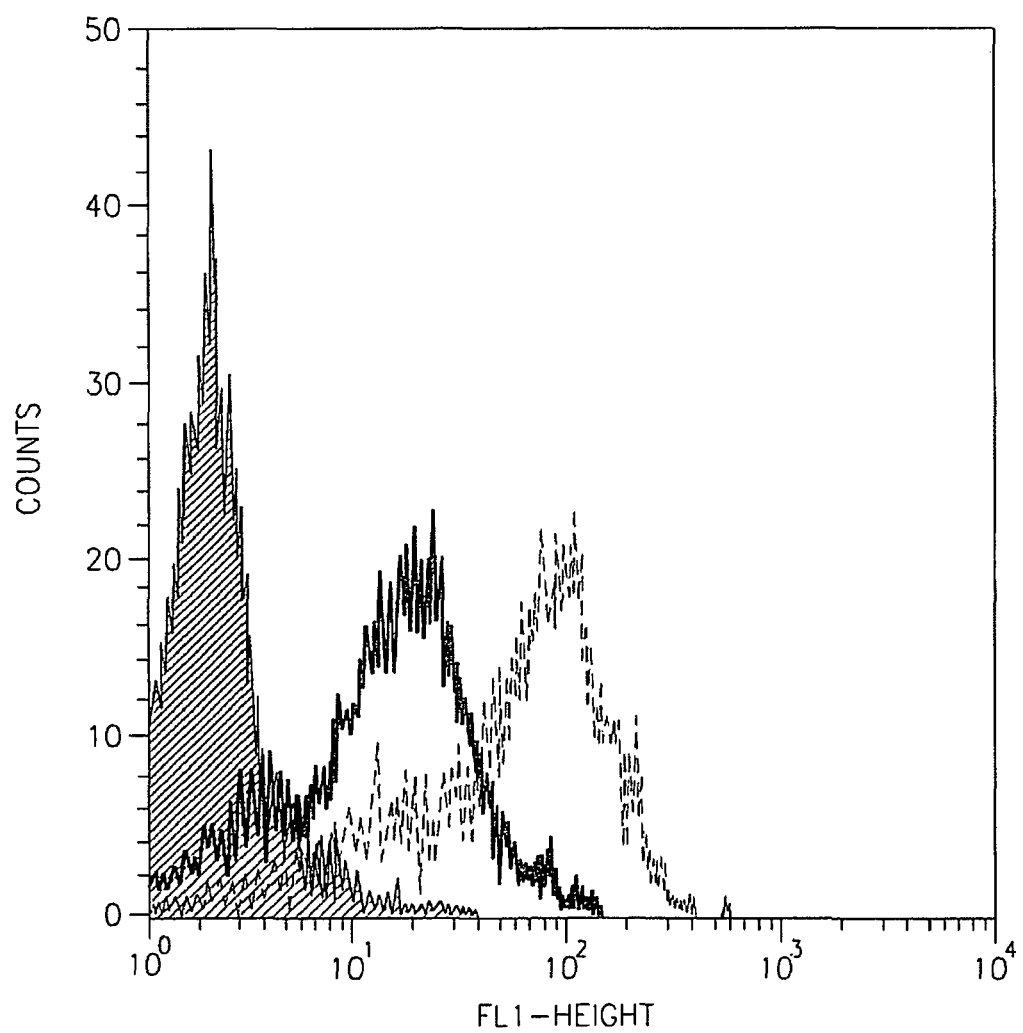
FIG. 3 demonstrates FACS analysis and demonstration of specific binding of the IT scFv/Fab35 VL-VH to TE671 RMS cells (red and green curve, fractions from the gradient chromotography).

These 4 scFv cDNAs were cloned into the ETA vector pBM-1.0, checked for proper ligation by sequencing and expressed in *E. coli* BL21DE3. The 4 expressed scFV-ETA proteins were purified and analysed by FACS analysis for binding capacity, using TE671 rhabdomyosarcoma (RMS) cells as targets (s. Materials and Methods). Among the 4 different ITs expressed, only the Fab35 derivative 35scFv/ VL-VH-ETA exhibited significant binding to TE671 cells (FIG. 3).

Figure 4:
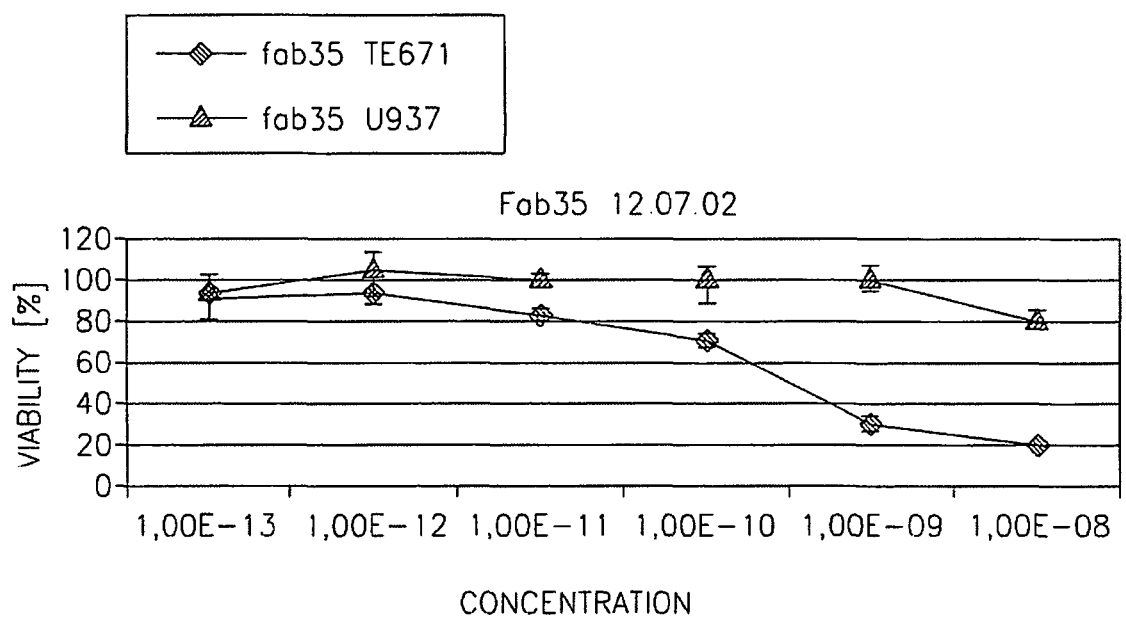
FIG. 4 demonstrates Colorimetric XTT cytotoxicity assay. Graphic presentation of the viability of TE671 RMS cells (green curve) and control U937 cells (blue curve) at different concentrations of IT scFv/Fab35 VL-VH on day 5 of a representative experiment.

The 35scFv$V_L$-$V_H$-ETA was further analysed for killing activity in an in vitro cytotoxicity assay using TE671 cells as targets. As shown in FIG. 4, the IT killed TE671 cells but not several AChR-negative control cell lines (IMR32, HL60, U937) in a dose-dependant manner. Killing activity of the IT could be prevented by blocking the IT binding site using "cold" (ETA-deficient) 35scFvVL-VH. In further assays, specific killing of other RMS cell lines (FLOH-1; RD;) was demonstrated.

Example 3

An AChR γ-Subunit-Targeting Immunotoxin Delays Tumour Development in a Mouse RMS Transplantation Model 35 scFvVL-VH-ETA was further investigated for its in vivo killing capacity using RD RMS cells as targets in a RMS transplantation mouse model. Toxicity tests revealed that intravenous injection of 10 μg IT per mouse had no apparent advers effect on the mice tested (n=10) in terms of mobility, weight development, and survival (up to 60 days). Therefore, this dose of IT was co-injected with RD cells ($10^7$ per mouse) (n=10) intravenously. Saline injections served as negative controls (n=4). Twice daily injections of 10 μg IT per mouse were repeated up to day 10. Tumour development was monitored by daily inspection and palpation. As shown in FIG. 5, 100% of mock injected mice exhibited palpable tumours day 7 of the experiment, and clearely visible subcutaneous tumours by day 10 (volume: 59+/−9mm$^3$). By contrast, no or minimal tumours were detectable in IT-injected mice by day 4 and the tumour remained generally invisible (but palpable in all cases) by day 10 (volume: 8+/−7 mm$^3$). Up to day 12 the tumours in the treated group were significantly smaller than in the controls (FIG. 5). After finishing the daily IT injections, however, subcutaneous tumours began to enlarge rapidly in the test group as well and were visible by day 14 in all animals, when the size of the tumours in test group was no longer signicantly different from the untreated controls (FIG. 5).

Example 4

IT Effects on Tumour Morphology and AChR Levels In-Vivo (to be Completed)

Mice were killed 20 days after the first injection. By histology, viable tumour was documented in all cases. Tumour volumes at that time were not significantly different in the treated (920+/−660 mm$^3$) and untreated control group (1544+/−342 mm$^3$) (p>0.10). By FACS analysis, no significant difference between the tumour cells of treated animals as compared to the control group could be seen (not shown). This finding was supported by immunohistochemistry, with tumours in the test and control group exhibiting expression of AChR γ-subunit at comparable levels and in a similar percentage of tumour cells. In agreement with these morphological finding RT-PCR revealed similar levels of AChR α- and γ-subunit mRNA expression in both groups of mice.

Example 5

Detection of Fetal AChR in Human RMS Biopsies Following Chemotherapy

Figure 6:
FIG. 6 shows the expression of the AchR γ-subunit in an embryonal RMS before (a) and after (b) chemotherapy. Overexpression and increased percentage of fetal AChR-positive tumour cells after chemotherapy in a three years old boy. Immunoperoxidase (x200).
Figure 6:
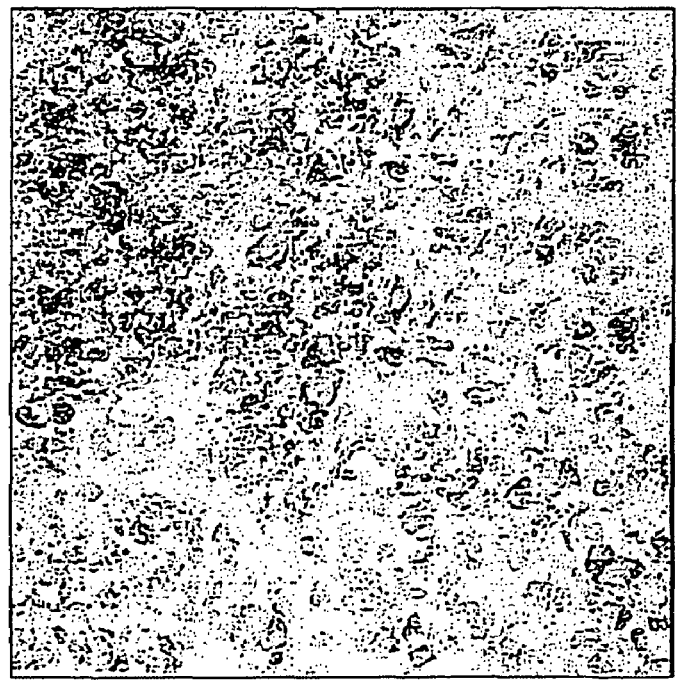

Since immunotoxin treatments in general can be improved by increasing expression levels of the target antigen on as many tumour cells as possible, we wondered whether chemotherapy might increase expression of fetal AChRs on RMS cells escaping current chemotherapies. As shown for a prototypic case in FIG. 6, vital RMS cells detected inside a second-look resection specimens (n=3) expressed high levels of fetal AChR on virtually 100% of tumour cells (FIG. 6a). By contrast, the same tumour prior to chemotherapy exhibited both less intense AChR expression levels and a significantly lower number of AChR(+) tumour cells (FIG. 6b).

Example 6

Antibodies Inhibiting Fetal AChR Function in MG

The records were searched for women with MG who had had children before their first available serum sample. We found twelve women with generalized MG who had had 1-3 children each by the time of sampling, which was before thymectomy or immunosuppressive treatment (Parous MG; see Table 1 in FIG. 11); in all but one case, MG presented during or after pregnancy. We compared the results with those of 12 women who had not had children at the time of sampling (Non-parous MG), 11 male MG patients and 12 healthy controls. Two AMC-M sera were used as positive controls. As expected, the age at MG onset was higher in the Parous MG than the Non-parous MG women (mean±SD; 30.7±7.8 compared with 19.9±5.3), but there was no substantial difference in the total levels of anti-AChR antibodies on routine testing (22.26±10.6 nM compared with 26.05±12.7 nM). Male MG patients were of a similar age to parous females (30.9±8.4) and with similar anti-AChR values (18.5±12.7). To assay the levels of fetal-AChR inhibitory antibodies, we measured the effects of the sera on agonist-induced $^{22}$Na flux into TE-671 cells. Healthy sera did not inhibit flux appreciably (0.02±0.58% compared to results in Hepes-Locke buffer alone). Inhibition of flux by the Parous MG sera was greater than that by the Non-parous (p=0.023; Mann Whitney one-tailed; FIG. 1) or male MG sera. These results suggest that pregnancy can influence the specificity of AChR antibodies in MG patients, and may initiate the response in some susceptible individuals.

Example 7

Cloning Anti-AChR Fabs from Thymic Combinatorial Libraries

In order to examine the clonal origins of fetal-specific AChR antibodies, we characterized Fabs cloned from unamplified VH/Vκ cDNA libraries prepared from thymic cells of AMC-M2 and AMC-M6, after screening 2.0-2.5×10$^5$ clones. It was relatively easy to detect AChR-specific plaques by blotting the expressed Fabs with $^{125}$I-αBuTx-AChR solubilized from human muscle, and to clone the positives by further rounds of screening (FIG. 8a); the results are summarized in Table 2. Fetal AChR inhibitory antibodies compete with one of the two α-BuTx-binding sites (Riemersma et al 1997), leaving the second site available for detection with $^{125}$I-α-BuTx. Therefore, in order to clone Fabs that might compete with α-BuTx for binding to the fetal AChR, we re-screened the AMC-M2 library with unlabeled muscle extract, allowing the AChR to bind before we applied the $^{125}$I-α-BuTx. A further 25 clones were thus isolated and two characterized in detail. We also prepared a parallel VH/Vλ library from AMC-M2 and isolated another 25 clones (Table 2 in FIG. 12).

Example 8

Specificity of AMC-M Fabs for Fetal AChR

Figure 8:
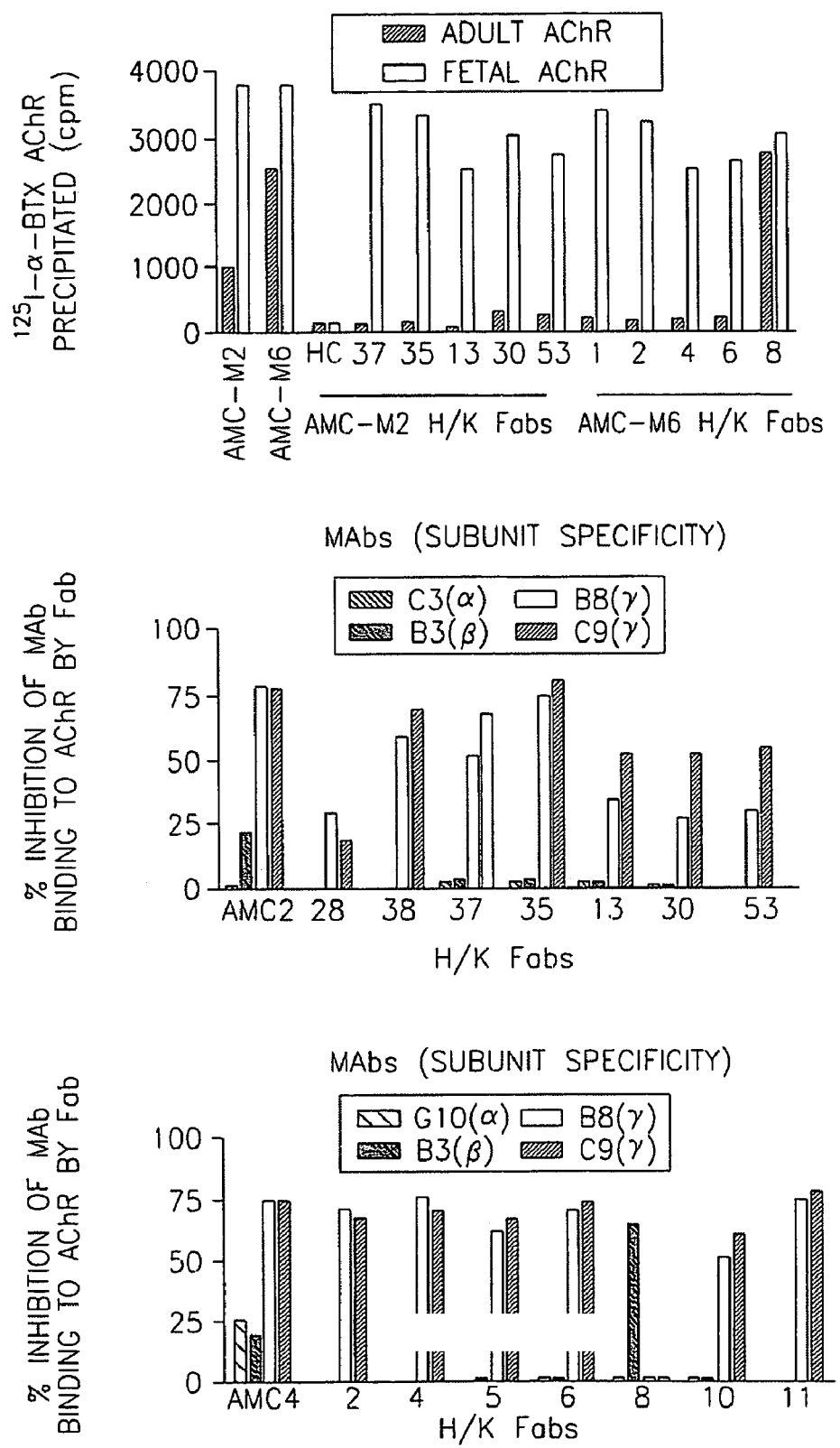
FIG. 8 shows AchR binding by Fab clones. Immunoprecipitation of $^{125}$I alpha BuTx by representative cloned Fabs from AMC-M2 (a) and from AMC-M6 (b).
Figure 9:
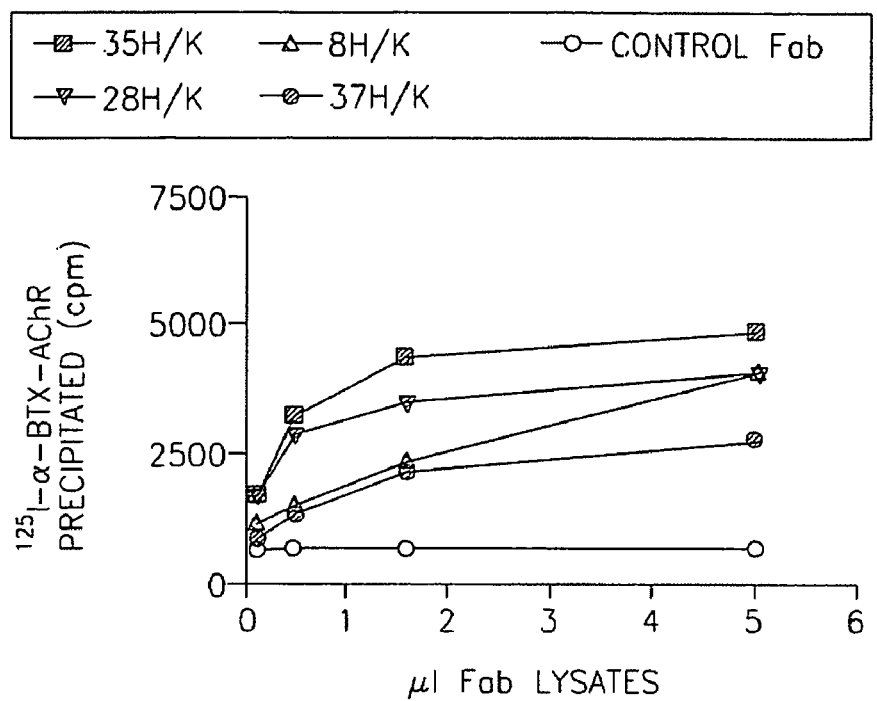
FIG. 9 shows the specificity of cloned Fabs. (a) reactivity of AMC-M2 and AMC-M6 serum antibodies and representative Fabs with adults and fetal AchR. (b) competition of AMC-M2 serum and Fab with mABs directed against the indicated AchR subunit. (c) competition of AMC-M6 serum and Fab with mABs directed against the indicated AchR subunit.
Figure 9:
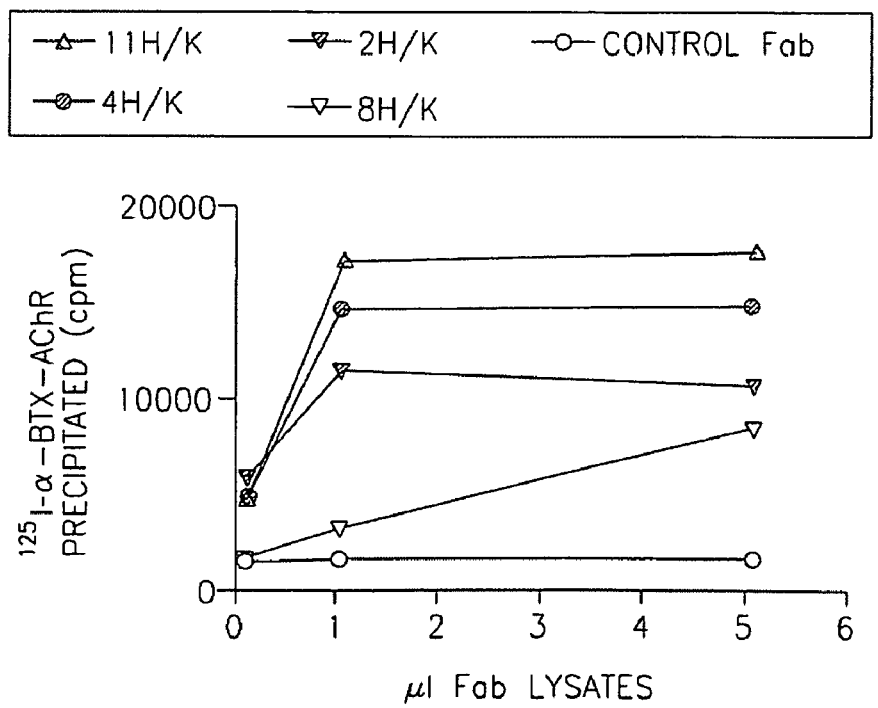

Both AMC-M2 and AMC-M6 libraries yielded Fabs that efficiently immunoprecipitated $^{125}$I-α-BuTx-human AChR, in most cases precipitating all of the available receptor. Examples of titrations of the Fabs are shown in FIGS. 8b and c; the efficient binding by monomeric Fabs of soluble AChR (at ~500 pM final concentration) indicates a high affinity. The muscle extracts used for screening and precipitations were from amputees with ischemic disease; although these have a preponderance of fetal over adult AChR (Vincent and Newsom-Davis 1984), antibodies to the α, β or δ subunits bind similarly to both isoforms (Tzartos et al 1998; Fostieri, Beeson and Tzartos 2000). We therefore tested the Fabs against AChR extracted from TE671 cells that express only fetal AChR, or from a TE671 subline that expresses predominantly (>90%) adult AChR (Beeson et al 1996). The two AMC-M sera preferred the fetal isoform, although they also showed some reactivity with adult AChR (FIG. 9a). However, all of the Fabs, with one exception (Fab 8H/K from AMC-M6), bound almost exclusively to fetal AChR. Even the low apparent reactivity with the adult AChR preparation could be due to the 10% contamination with fetal AChR (Beeson et al 1996).

To confirm this striking finding, we also tested the Fabs' ability to block the binding of mAbs specific for human fetal AChR γ subunits. Both AMC-M2 and AMC-M6 serum antibodies blocked binding of each of the two mAbs specific for fetal AChR (FIGS. 3b and c), as did all the Fabs except 8K from AMC-M6, which instead blocked binding of the mAb with β subunit-specificity (FIG. 3c). These experiments confirm the high affinity for fetal AChR of the Fabs and most of the serum antibodies, and their probable γ subunit-specificity.

It was also important to test the Fabs for inhibition of fetal AChR ion channel function. Disappointingly, only Fab 35K from AMC-M2 showed appreciable activity and that only at relatively high Fab concentrations (50% inhibition at 100 µl of Fab). There was no effect on adult AChR (data not shown). In parallel experiments, cross-linking the cloned Fabs with secondary antibodies did not increase the degree of inhibition. Indeed, inhibition of function did not require divalent antibodies, since it was readily measurable with monovalent Fabs prepared from both donors' serum Ig (data not shown).

Example 9

Sequences of the AMC-M2 Fab VH and Vκ Genes

The V-genes were sequenced and compared with those in the human Ig VBASE directory (Tomlinson et al 1997) to identify both the closest germline sequence and the number of somatic mutations (Table 3 in FIG. 13). All the AMC-M2 Fabs were specific for fetal AChR and used the same VH3-07/D/JH6b combination, regardless both of the screening procedure used to identify them (Table 2 in FIG. 12) and of their exact κ (Table 3 in FIG. 13) or λ light chain partner (not shown). They had the same CDR3 length and the majority shared 32 'consensus' VH mutations, demonstrating a common clonal origin from a previously-mutated progenitor. Replacement:silent (R:S) ratios were higher in the first two hypervariable (CDR) loops than in the framework regions (FWR), strongly suggesting antigen-driven selection for antibody specificity/affinity.

By contrast, the AMC-M2 kappa light sequences were heterogeneous; despite their similar binding specificity, these Fabs used a variety of Vκ (Table 3 in FIG. 13), which varied substantially both in numbers of mutations and R:S ratios. Although two Fabs used the Vκ 02/12 gene, their different Jκ usage demonstrates that they are independent gene rearrangements. This contrasting VH restriction and Vκ diversity suggests that the heavy chain was primarily responsible for the fetal AChR-binding specificity.

Example 10

Recurring VH and Vκ Usage by AMC-M6 Fabs

Table 3 also summarizes the genes encoding the second donor's anti-AChR Fabs. Fab 8H/K is the first human AChR β subunit-specific autoantibody to be cloned. It uses the relatively uncommon VH4-61 gene in combination with the commonly expressed VK1 02/12 Vκ gene. Both the heavy and light chains are highly mutated, with higher R:S ratios in the CDR than the FWR regions (Table 3 in FIG. 13). One of the fetal AChR-specific Fabs (Fab 1H/K) used a highly mutated VH3-23/DH3.3/JH6b plus a Vκ4 B3/Jκ 3 gene (Table 3 in FIG. 13). All of the others used the same pair of VH3-21/D/JH5b heavy and Vκ 02/12 light chain genes, again with Jκ4 (Table 3); the frequency of base differences between these sequences is significantly above the PCR error rate (22), but the VHs and Vκs are clearly clonally-related.

The extent of somatic mutation shows that each is clearly derived from a highly mutated progenitor (with 44 consensus substitutions in the VH and 25 in the Vκ). The R:S ratios for the heavy chain gene are moderate, because the number of VH mutations approaches saturation (often 2 or even 3 per codon). Their closest germline counterparts and their clonal relationships are shown in FIG. 10; the pattern is essentially similar for the VH sequences of the AMC-M2 Fabs (not shown). In the genealogical trees for both heavy and light chains, the branching patterns, with variable numbers of successive mutations separating each sequence, are clear evidence of further antigen-driven clonal proliferation and somatic mutation; moreover exach stems from an already-mutated progenitor. Notably also, since neither this heavy nor this light chain was found with other partners, they could both be derived from the same progenitor B cell.

Example 11

Convergent Mutations Suggesting Common Fetal AChR-Specific Selection Processes

We saw recurring replacements in the three independent fetal AChR-specific VH3 genes and especially in the Vκ 02/12 sequences. In brief, there was a CDR1 $^{31}$S→T substitution in all VH3 Fabs from AMC-M2 and AMC-M6. Even more strikingly, among the Vκ 02/12 light chains, AMC-M2 13K and the majority of the AMC-M6 Fabs not only use Jκ4 but also have common $^{22}$T→S, $^{27}$Q→E, $^{28}$S→T and $^{53}$S→T replacements. The former three contribute to the CDR1 to form a $^{22}$SRASET$^{28}$ motif that is found in only two other human κ sequences in GenBank. Moreover, these recurring H and L chain mutations were not seen in another fetal AChR-specific Fab from a non-parous EOMG female (Farrar et al 1997) or in the very different AChR β-specific Fab-8 from AMC-M6 (data not shown).

What is claimed is:

1. An immunotoxin directed at fetal AChRγ, comprising a single chain scFv35-$V_L$-$V_H$, wherein said scFv35-$V_L$-$V_H$ comprises a heavy chain V ($V_H$) comprising a peptide encoded by a nucleotide sequence set forth in SEQ ID NO: 25, SEQ ID NO: 26, SEQ ID NO: 27, SEQ ID NO: 28, SEQ ID NO: 29, SEQ ID NO: 30 or SEQ ID NO: 31, wherein said scFv35-$V_L$-$V_H$ comprises a peptide as set forth in SEQ ID NO: 13, and wherein said immunotoxin is directed at fetal AchRγ.

2. A method of treating a patient with soft tissue tumour comprising the step of exposing the patient to an immunotoxin according to claim 1.

3. The method of claim 2, wherein said soft tissue tumour comprises nicotinic AChR.

4. The method of claim 2, wherein said soft tissue tumour comprises fetal AChR.

5. A method of treating a patient with sarcoma comprising the step of exposing the patient to an immunotoxin according to claim 1.

6. The method of claim 5, wherein said sarcoma is Rhabdomyosarcoma (RMS).

7. A method of killing cells comprising the step of contacting the cells with an immunotoxin according to claim 1.

8. The method of claim 7, wherein said cells are RMS cells.

9. The method of claim 7, wherein said cells comprising nicotinic AChR.

10. The method of claim 7, wherein said cells comprising fetal AChR.

11. The method of claim 7, wherein prior to said step of contacting the cells with immunotoxin according to claim 1, the cells are contacted with a chemotherapeutic agent.

12. A method of delaying the development of RMS in a patient comprising the step of exposing the patient to the immunotoxin of claim 1.

13. A method of delaying the development of RMS cells, comprising the step of contacting the RMS cells with an immunotoxin according to claim 1.

14. A pharmaceutical composition comprising the immunotoxin of claim 1, or the scFv35-$V_L$-$V_H$ of claim 1.

15. A method according to claim 11, wherein said chemotherapeutic agent is selected from the group consisting of a DNA-interactive agent, alkylating agent, antimetabolite, tubulin-interactive agent, hormonal agent, Asparaginase and hydroxyurea.

16. A method according to claim 11, wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole carbamate and Plicamycin.

17. The immunotoxin of claim 1, wherein said scFv-$V_L$-$V_H$ comprises a light chain V ($V_L$) comprising a peptide encoded by a nucleotide sequence set forth in SEQ ID NO.: 42, SEQ ID NO.: 43, SEQ ID NO.: 44, SEQ ID NO.: 45, SEQ ID NO.: 46, SEQ ID NO.: 47, SEQ ID NO.: 48, SEQ ID NO.: 49 or SEQ ID NO.:50.

18. The immunotoxin of claim 1, further comprising a toxic domain comprising a toxic polypeptide.

19. The immunotoxin of claim 18, wherein said toxic polypeptide is ricin, Pseudomonas exotoxin, Pseudomonas exotoxin A (ETA), bryodin, gelonin, α-sarcin, aspergillin, restrictocin, angiogenin, saporin, abrin, pokeweed antiviral protein or diphtheria toxin, or a functional fragment thereof.

20. The immunotoxin of claim 1, wherein said immunotoxin comprises a Pseudomonas exotoxin A-based single chain Fv immunotoxin, 35-scFV35$V_L$-$V_H$-ETA.

21. The immunotoxin of claim 18, wherein said scFv-$V_L$-$V_H$ comprises a heavy chain V ($V_H$) comprising peptide encoded by a nucleotide sequence set forth in SEQ ID NO: 29 and a light chain V ($V_L$)) comprising the peptide encoded by the nucleotide sequence set forth in SEQ ID NO: 46.

\* \* \* \* \*

SEQUENCE LISTING

<160> NUMBER OF SEQ ID NOS: 86

<210> SEQ ID NO 1
<211> LENGTH: 55
<212> TYPE: DNA
<213> ORGANISM: Artificial Sequence
<220> FEATURE:
<223> OTHER INFORMATION: scFv/Fab35 VH 5prime Sfi I

<400> SEQUENCE: 1
agtctaaggt tcggcccagc cggcctcggg gggcgacttg gtccagccgg ggggg    55

<210> SEQ ID NO 2
<211> LENGTH: 55
<212> TYPE: DNA
<213> ORGANISM: Artificial Sequence
<220> FEATURE:
<223> OTHER INFORMATION: scFv/Fab38 VH 5prime Sfi I

<400> SEQUENCE: 2
agtctaacgt tcggcccagc cggcctcggg gggaggcgtg gtccagccgg ggggg    55

<210> SEQ ID NO 3
<211> LENGTH: 66
<212> TYPE: DNA
<213> ORGANISM: Artificial Sequence
<220> FEATURE:
<223> OTHER INFORMATION: scFv/Fab35/38 VH 3prime Linker

<400> SEQUENCE: 3
gccacccgac ccaccaccgc ccgagccacc gccacctgga gagacggtga ccgttgtccc    60
ttggcc                                                                66

<210> SEQ ID NO 4
<211> LENGTH: 54
<212> TYPE: DNA
<213> ORGANISM: Artificial Sequence
<220> FEATURE:
<223> OTHER INFORMATION: scFv/Fab35/38 VL 5prime Linker

<400> SEQUENCE: 4
ggctcgggcg gtggtgggtc gggtggcggc ggatcagtga tgacccagtc tcca    54

<210> SEQ ID NO 5
<211> LENGTH: 36
<212> TYPE: DNA
<213> ORGANISM: Artificial Sequence
<220> FEATURE:
<223> OTHER INFORMATION: scFv/Fab35 VL 3prime Not I

<400> SEQUENCE: 5
tgctggtgcg gccgctttga tctccagctt ggtccc    36

<210> SEQ ID NO 6
<211> LENGTH: 36
<212> TYPE: DNA
<213> ORGANISM: Artificial Sequence
<220> FEATURE:
<223> OTHER INFORMATION: scFv/Fab38 VL 3prime Not I

<400> SEQUENCE: 6
tgctgctgcg gccgccgtga tctccagctt ggtccc    36

<210> SEQ ID NO 7

```
<211> LENGTH: 45
<212> TYPE: DNA
<213> ORGANISM: Artificial Sequence
<220> FEATURE:
<223> OTHER INFORMATION: scFv/Fab35/38 VL 5prime Sfi I

<400> SEQUENCE: 7
atggctcagg gttcggccca gccggccgtg atgacccagt ctcca                    45

<210> SEQ ID NO 8
<211> LENGTH: 57
<212> TYPE: DNA
<213> ORGANISM: Artificial Sequence
<220> FEATURE:
<223> OTHER INFORMATION: scFv/Fab35 VL 3prime Linker

<400> SEQUENCE: 8
gccacccgac ccaccaccgc ccgagccacc gccacctttg atctccagct tggtccc       57

<210> SEQ ID NO 9
<211> LENGTH: 57
<212> TYPE: DNA
<213> ORGANISM: Artificial Sequence
<220> FEATURE:
<223> OTHER INFORMATION: scFv/Fab38 VL 3prime Linker

<400> SEQUENCE: 9
gccacccgac ccaccaccgc ccgagccacc gccacccgtg atctccagct tggtccc       57

<210> SEQ ID NO 10
<211> LENGTH: 66
<212> TYPE: DNA
<213> ORGANISM: Artificial Sequence
<220> FEATURE:
<223> OTHER INFORMATION: scFv/Fab35 VH 5prime Linker

<400> SEQUENCE: 10
ggctcgggcg gtggtgggtc gggtggcggc ggatcatcgg ggggcgactt ggtccagccg    60
gggggg                                                               66

<210> SEQ ID NO 11
<211> LENGTH: 66
<212> TYPE: DNA
<213> ORGANISM: Artificial Sequence
<220> FEATURE:
<223> OTHER INFORMATION: scFv/Fab38 VH 5prime Linker

<400> SEQUENCE: 11
ggctcgggcg gtggtgggtc gggtggcggc ggatcatcgg ggggaggcgt ggtccagccg    60
gggggg                                                               66

<210> SEQ ID NO 12
<211> LENGTH: 45
<212> TYPE: DNA
<213> ORGANISM: Artificial Sequence
<220> FEATURE:
<223> OTHER INFORMATION: scFv/Fab35/38 VH 3prime Not I

<400> SEQUENCE: 12
tgctgctgcg gccgctggag agacggtgac ggttgtccct ggcc                     45

<210> SEQ ID NO 13
<211> LENGTH: 22
<212> TYPE: PRT
<213> ORGANISM: Homo sapiens
```

-continued

```
<400> SEQUENCE: 13

Val Arg Arg Tyr Gly Pro Ser Thr Leu Ser Pro Phe Thr Trp Lys Asp
1               5                   10                  15

Asn His Tyr Ala Met Asp
            20

<210> SEQ ID NO 14
<211> LENGTH: 22
<212> TYPE: PRT
<213> ORGANISM: Homo sapiens

<400> SEQUENCE: 14

Val Arg Gln Phe Gly Ala Leu Pro Pro Asn Gln Tyr Asn Phe Asp Glu
1               5                   10                  15

Leu His Tyr Ala Met Asp
            20

<210> SEQ ID NO 15
<211> LENGTH: 10
<212> TYPE: PRT
<213> ORGANISM: Homo sapiens

<400> SEQUENCE: 15

Gly Arg Gly Lys Phe Glu Leu Leu Asp Phe
1               5                   10

<210> SEQ ID NO 16
<211> LENGTH: 14
<212> TYPE: PRT
<213> ORGANISM: Homo sapiens

<400> SEQUENCE: 16

Val Val Asn Tyr Gln Arg Ser Gln Val Gly Trp Phe Asp Pro
1               5                   10

<210> SEQ ID NO 17
<211> LENGTH: 18
<212> TYPE: PRT
<213> ORGANISM: Homo sapiens

<400> SEQUENCE: 17

Glu Trp Gly Ser Arg Phe Ile Thr Thr Phe Arg Gly Leu Pro His Phe
1               5                   10                  15

Asp Leu

<210> SEQ ID NO 18
<211> LENGTH: 18
<212> TYPE: PRT
<213> ORGANISM: Homo sapiens

<400> SEQUENCE: 18

Glu Trp Gly Ser Arg Phe Ile Thr Ser Phe Arg Gly Leu Pro His Phe
1               5                   10                  15

Asp Leu

<210> SEQ ID NO 19
<211> LENGTH: 18
<212> TYPE: PRT
<213> ORGANISM: Homo sapiens

<400> SEQUENCE: 19

Glu Trp Gly Ser Arg Phe Ile Thr Pro Phe Arg Gly Leu Pro His Phe
1               5                   10                  15
```

Asp Leu

<210> SEQ ID NO 20
<211> LENGTH: 9
<212> TYPE: PRT
<213> ORGANISM: Homo sapiens

<400> SEQUENCE: 20

Gln Gln Ser Tyr Asn Thr Pro Asn Thr
1               5

<210> SEQ ID NO 21
<211> LENGTH: 9
<212> TYPE: PRT
<213> ORGANISM: Homo sapiens

<400> SEQUENCE: 21

Gln Gln Tyr Ser Gly Phe Ser Trp Thr
1               5

<210> SEQ ID NO 22
<211> LENGTH: 9
<212> TYPE: PRT
<213> ORGANISM: Homo sapiens

<400> SEQUENCE: 22

Gln Gln Ser Tyr Leu Thr Pro Leu Thr
1               5

<210> SEQ ID NO 23
<211> LENGTH: 9
<212> TYPE: PRT
<213> ORGANISM: Homo sapiens

<400> SEQUENCE: 23

Gln Gln Ser Tyr Thr Thr Pro Leu Thr
1               5

<210> SEQ ID NO 24
<211> LENGTH: 9
<212> TYPE: PRT
<213> ORGANISM: Homo sapiens

<400> SEQUENCE: 24

Gln Gln Ser Phe Thr Thr Pro Leu Thr
1               5

<210> SEQ ID NO 25
<211> LENGTH: 381
<212> TYPE: DNA
<213> ORGANISM: Homo sapiens

<400> SEQUENCE: 25

```
gagtctgggg gcgacttggt ccagccgggg gggtccctga gagtctcctg tgtagcctct      60
ggatttacat ttaggaccta tgtgatgaac tgggtccgcc aggctccagg aaagggctg     120
gagtgggtgg cccacataag tccagaggga actgaagaat actatgcgga ctctgtgaag    180
ggccgattta ccatctccag agacaacgcg gagaattcag tatttctgca aatgaacagt    240
ctgagaggcg aggacacggc tgtgtattat tgcgcgagag tccgacgcta tggtccctct    300
acactcagtc cgttcacctg gaaggacaat cactacgcca tggacgtctg gggccaaggg    360
accacggtca ccgtctcttc a                                              381
```

<210> SEQ ID NO 26
<211> LENGTH: 381
<212> TYPE: DNA
<213> ORGANISM: Homo sapiens

<400> SEQUENCE: 26

```
gagtctgggg gcgacttggt ccagccgggg gggtccctga gagtctcctg tgtagcctct      60
ggatttacat ttaggaccta tgtgatgaac tgggtccgcc aggctccagg aaaggggctg     120
gagtgggtgg cccacataag tccagaggga actgaagaat actatgcgga ctctgtgaag     180
ggccgattta ccatctccag agacaacgcg aagaattcag tatttctgca aatgaacagt     240
ctgagaggcg aggacacggc tgtgtattat tgcgcgagag tccgacgcta tggtccctct     300
acactcagtc cgttcacctg gaaggacaat cactacgcca tggacgtctg gggccaaggg     360
accacggtca ccgtctcttc a                                               381
```

<210> SEQ ID NO 27
<211> LENGTH: 381
<212> TYPE: DNA
<213> ORGANISM: Homo sapiens

<400> SEQUENCE: 27

```
gagtctgggg gcgacttggt ccagccgggg gggtccctga gagtctcctg tgtagcctct      60
ggatttacat ttaggaccta tgtgatgaac tgggtccgcc aggctccagg aaaggggctg     120
gagtgggtgg cccacataag tccagaggga actgaagaat actatgcgga ctctgtgaag     180
ggccgattta ccatctccag agacaacgcg aagaattcag tatttctgca aatgaacagt     240
ctgagaggcg aggacacggc tgtgtattat tgcgcgagag tccgacgcta tggtccctct     300
acactcagtc cgttcacctg gaaggacaat cactacgcca tggacgtctg gggccaaggg     360
accacggtta ccgtctcttc a                                               381
```

<210> SEQ ID NO 28
<211> LENGTH: 381
<212> TYPE: DNA
<213> ORGANISM: Homo sapiens

<400> SEQUENCE: 28

```
gagtcggggg gcgacttggt ccagccgggg gggtccctga gagtctcctg tgtagcctct      60
ggatttacat ttaggaccta tgtgatgaac tgggtccgtc aggctccagg aaaggggctg     120
gagtgggtgg cccacataag tccagaggga actgaagaat actatgcgga ctctgtgaag     180
ggccgattta ccatctccag agacaacgcg aagaattcag tatttctgca aatgaacagt     240
ctgagaggcg aggacacggc tgtgtattat tgcgcgagag tccgacgcta tggtccctct     300
acactcagtc cgttcacctg gaaggacaat cactacgcca tggacgtctg gggccaaggg     360
accacggtca ccgtctcttc a                                               381
```

<210> SEQ ID NO 29
<211> LENGTH: 381
<212> TYPE: DNA
<213> ORGANISM: Homo sapiens

<400> SEQUENCE: 29

```
gagtcggggg gcgacttggt ccagccgggg gggtccctga gagtctcctg tgtagcctct      60
ggatttacat ttaggaccta tgtgatgaac tgggtccgcc aggctccagg aaaggggctg     120
gagtgggtgg cccacataag tccagaggga actgaagaat actatgcgga ccctgtgaag     180
```

```
ggccgattta ccatctccag agacaacgcg aagaattcag tatttctgca aatgaatagt    240
ctgagaggcg aggacacggc tgtgtattat tgcgcgagag tccgacgcta tggtccctct    300
acgctcagtc cgttcacctg aaggacaat cactacgcca tggacgtctg gggccaaggg    360
acaacggtca ccgtctctcc a                                             381

<210> SEQ ID NO 30
<211> LENGTH: 381
<212> TYPE: DNA
<213> ORGANISM: Homo sapiens

<400> SEQUENCE: 30
gagtcggggg gcgacttggt ccagccgggg gggtccctga gagtctcctg tgtagcctct    60
ggatttacat ttaggaccta tgtgatgaac tgggtccgcc aggctccagg aaaggggctg   120
gagtgggtgg cccacataag tccagaggga actgaagaat actatgcgga ctctgtgaag   180
ggccgattta ccatctccag agacaacgcg aagaattcag tatttctgca aatgaatagt   240
ctgagaggcg aggacacggc tgtgtattat tgcgcgagag tccgacgcta tggtccctct   300
acactcagtc cgttcacctg aaggacaat cactacgcca tggacgtctg gggccaaggg    360
acaacggtca ccgtctctcc a                                             381

<210> SEQ ID NO 31
<211> LENGTH: 381
<212> TYPE: DNA
<213> ORGANISM: Homo sapiens

<400> SEQUENCE: 31
gagtcggggg gcgacttggt ccagccgggg gggtccctga gagtctcctg tgtagcctct    60
ggatttacat ttaggaccta tgtgatgaac tgggtccgcc aggctccagg aaaggggctg   120
gagtgggtgg cccacataag tccagaggga actgaagaat actatgcgga ctctgtgaag   180
ggccgattta ccatctccag agacaacgcg atgaattcag tatttctgca aatgaatagt   240
ctgagaggcg aggacacggc tgtgtattat tgcgcgagag tccgacgcta tggtccctct   300
acactcagtc cgttcacctg aaggacaat cactacgcta tggacgtctg gggccaaggg    360
acaacggtca ccgtctctcc a                                             381

<210> SEQ ID NO 32
<211> LENGTH: 381
<212> TYPE: DNA
<213> ORGANISM: Homo sapiens

<400> SEQUENCE: 32
gagtcggggg gaggcgtggt ccagccgggg gggtccctga cagtctcctg taaagcctct    60
ggatatgttt tcaggaccttt tctcatgact tgggtccgcc tggctccagg agggggctg   120 gagtgggtgg ccaacataag tccagcggga actgagaaac attatatgga ctctgttgag   180
gggcgattct ccatctccag agacaatgcc cagaactcac tctttctgca aatgaacggc   240
ctgagaggcg aagacacggc tctctatttt tgtgccagag tccgacaatt tggtgccctt   300
cctcccaatc aatataactt tgatgaactc cactacgcga tggacctctg gggccaaggg   360
accgcggtca tcgtctcctc a                                             381

<210> SEQ ID NO 33
<211> LENGTH: 381
<212> TYPE: DNA
<213> ORGANISM: Homo sapiens
```

<400> SEQUENCE: 33

```
gagtcggggg gcgacttggt ccagccgggg gggtccctga gagtctcctg tgtagcctct      60
ggatttacat ttaggaccta tgtgatgaac tgggtccgcc aggctccagg aaaggggctg     120
gagtgggtgg cccacataag tccagcggga actgaagaat actatgcgga ctctgtgaag     180
ggccgattta ccatctccag agacaatgcc cagaactcac tctttctgca aatgaacggc     240
ctgagaggcg aagacacggc tctctatttt tgtgccagag tccgacaatt tggtgccctt     300
cctcccaatc aatataactt tgatgaactc cactacgcga tggacctctg ggccaaggg      360
accgcggtca tcgtctcttc a                                               381
```

<210> SEQ ID NO 34
<211> LENGTH: 369
<212> TYPE: DNA
<213> ORGANISM: Homo sapiens

<400> SEQUENCE: 34

```
ctcgagtcgg ggggaggcct ggtcaagcct gaggggtccc taagactctc ctgtattgcc      60
tctggattca cctttaatac ctacaatatg aattgggtcc gtcagcctcc agggaagggc     120
ctggaatggg tcgcttccat aacagcgact agcagtcaca cagagtacgg aagctccgtt     180
gcgggacgct tcaccatctc cagagacaac accaagaagt ctctttatct agacatgacc     240
cgtctgagag ccgaagacac ggcactttat ttttgtgttc gagagtgggg aagtagattc     300
atcactacgt ttcggggcct tcctcacttc gacctctggg gccagggagc cctggtcatc     360
gtctcgtca                                                             369
```

<210> SEQ ID NO 35
<211> LENGTH: 369
<212> TYPE: DNA
<213> ORGANISM: Homo sapiens

<400> SEQUENCE: 35

```
ctcgagtcgg ggggaggcct ggtcaagcct gaggggtccc taagactctc ctgtattgcc      60
tctggattca cctttaatac ctacaatatg aattgggtcc gtcagcctcc agggaaggga     120
ctggaatggg tcgcttcaat aacagcgact agcagtcaca cagagtacgg aggctccgtt     180
gcgggacgct tcaccatctc cagagacaac gccaagaagt ctctttatct agacatgacc     240
cgtctgagag ccgaagacac ggcactttat ttttgtgttc gagagtgggg gagtagattc     300
atcactacgt ttcggggcct tcctcacttc gacctctggg gccagggagc cctggtcatc     360
gtctcgtca                                                             369
```

<210> SEQ ID NO 36
<211> LENGTH: 369
<212> TYPE: DNA
<213> ORGANISM: Homo sapiens

<400> SEQUENCE: 36

```
ctcgagtctg ggggaggcct ggtcaagcct gaggggtccc taaggctctc ctgtcttgcc      60
tctggattca cctttaatac ctacaatatg aattgggtcc gtcagcctcc agggaaggga     120
ctggaatggg tcgcttcaat aacagcgact agcagtcaca cagagtacgg aggctccgtt     180
gcgggacgct tcaccatctc cagagacaac accaagaagt ctctttatct agacatgacc     240
cgcctgagag ccgaagacac ggcactttat ttttgtgttc gagaatgggg aagcagattc     300
atcacaacat ttcggggcct tcctcacttc gacctctggg gccagggagc cctggtcatc     360
```

```
gtctcgtca                                                              369

<210> SEQ ID NO 37
<211> LENGTH: 369
<212> TYPE: DNA
<213> ORGANISM: Homo sapiens

<400> SEQUENCE: 37
ctcgagtctg ggggaggcct ggtcaagcct gacgggtccc gaaggctctc ctgtgttgcc        60
tctggattca cctttaacac ctacaatatg aattgggtcc gtcagcctcc agggaaggga       120
ctggaatggg tcgcttcaat aacgtcgact agcagtcata cagagtacgg aggctccgtt       180
gcgggccgct tcaccatctc cagagacaac accaagaagt ctctttatct ggacatgacc       240
cgtctgagag ccgaggacac ggcactttat ttttgtgttc gagagtgggg aagtagattc       300
atcactacgt ttcggggcct tcctcatttc gacctctggg gccagggagc cctggtcatc       360
gtctcgtca                                                              369

<210> SEQ ID NO 38
<211> LENGTH: 369
<212> TYPE: DNA
<213> ORGANISM: Homo sapiens

<400> SEQUENCE: 38
ctcgagtctg ggggaggcct ggtcaagcct gaggggtccc taagactctc ctgtattgcc        60
tctggattca cttttaatac ctacaatatg aattgggtcc gtcaaactcc agggaaggga       120
ctggagtggg tcgcatcaat aagtacgact agcagtcaca cagagtacac agactccgtt       180
gcggggcgct tcaccatctc cagagacaac accaagaagt ctctttatct agacatgacc       240
agcctgagag ccgaagacac ggcactttat tattgtgtgc gagaatgggg cagtagattc       300
atcacttcgt ttcggggcct tcctcacttt gacctctggg gccagggagc cctggtcatc       360
gtctcctca                                                              369

<210> SEQ ID NO 39
<211> LENGTH: 369
<212> TYPE: DNA
<213> ORGANISM: Homo sapiens

<400> SEQUENCE: 39
ctcgagtcgg ggggaggcct ggtcaagcct gaggggtccc taagactctc ctgtgttgcc        60
tctggattca cgtttaacac ctacaacatg aattgggtcc gtcagcctcc agggaagggc       120
ctggagtggg tcgcctcaat aacaacgact agcagtcata cagagtatgg aggctctgtt       180
gcggagcggt tcagcatctc cagagacaac accaagaagt ccctgtatct agacatgacc       240
cgtctgagag ccgaagacac ggcactttat ttttgtgttc gagaatacgg aagtagattt       300
atcactccat ttcggggcct tcctcacttt gacctctggg gcctgggagc ccgggtcatc       360
gtctcgtca                                                              369

<210> SEQ ID NO 40
<211> LENGTH: 348
<212> TYPE: DNA
<213> ORGANISM: Homo sapiens

<400> SEQUENCE: 40
ctcgagtcgg gcccaggact gctaaagcct tcacagaccc tgtccctcac ctgctctgtc        60
tctggtgcct ccctcagtcg tggtgcatac ttctggactt ggatccggca gccggccggg       120
```

```
aagggactgg aatggattgg tcgtgtctat accattgaga acaccgtcta caacccctcc    180
ctcaggagtc gagtcaccat gtctgtcgac acgtccaaga acttattctc cctggacctg    240
cgctctgtca cctccgcaga cacggccgtc tattattgtg cgagagggag ggggaagttc    300
gaactacttg acttctgggg ccagggaatc ccggtcaccg tctcgtca                 348
```

<210> SEQ ID NO 41
<211> LENGTH: 357
<212> TYPE: DNA
<213> ORGANISM: Homo sapiens

<400> SEQUENCE: 41

```
ctcgagtctg ggggaggctt ggtacagcca gggcggtccc tgagactctc ctgtgcagcc    60
tctggattca cctttagcac ctatgccctg gcctgggtcc gccaggctcc agggaagggg    120
ctggagtggg tctcagttat caataatagt ggtggcagca catattatgc agtctccgtg    180
agcggccggt tcgccatctc cagagataat tccaagaaca cgctgtatct agagatgcgc    240
agcctgagag ccgaggacac ggccgtctat ttctgtgcca aagggaagga cggactgatt    300
atactacccg cgctatggac cgtctggggc caagggaccg cggtcaccgt gtcctca       357
```

<210> SEQ ID NO 42
<211> LENGTH: 322
<212> TYPE: DNA
<213> ORGANISM: Homo sapiens
<220> FEATURE:
<221> NAME/KEY: misc_feature
<222> LOCATION: (71)..(71)
<223> OTHER INFORMATION: n is a, c, g, or t

<400> SEQUENCE: 42

```
gagctcgtga tgacccagtc tccatcttcc gtgtctgtat ctctaggaga cagaatcacc    60
atcacttgtc ncgcgagtca aaatattagc aactggttag cctggtatca gcagaaacca    120
gggaaagccc ctaagctcct gatctattct gcatccagtt tgcaaagtgg agtcccatca    180
aggttcagcg gcagtgggtc tgggacagat ttcactctca ccatcagcag cctgcagcct    240
gaagattttg caacttacta ttgtcaacag tctaacagtt tcccccggac gttcggccaa    300
gggaccaagg tggaaatcaa ac                                              322
```

<210> SEQ ID NO 43
<211> LENGTH: 322
<212> TYPE: DNA
<213> ORGANISM: Homo sapiens

<400> SEQUENCE: 43

```
gagctcgtga tgacccagtc tccatcctcc ctgtctgctt ctgttgggga cagaataacc    60
atctcttgcc gggcaagtga gaccattagt cattacttaa attggtatca gcagaatcca    120
gggaaagccc caaagctcct gatctttggt gcatccactt tggagagtgg ggtcccctca    180
aggttcagtg gcgatggatc tgggacagat ttcactctca ccatcgacag cctccaacct    240
gaagattttg caacgtacta ctgtcaacag ggttacagtt cttcgctcac tttcggcgga    300
gggaccaagg tggagattaa ag                                              322
```

<210> SEQ ID NO 44
<211> LENGTH: 328
<212> TYPE: DNA
<213> ORGANISM: Homo sapiens
<220> FEATURE:
<221> NAME/KEY: misc_feature
<222> LOCATION: (292)..(292)

```
<223> OTHER INFORMATION: n is a, c, g, or t

<400> SEQUENCE: 44
gagctcgtga tgacccagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcatcag tataataact ggcttcggaa anacacttttt   300 ggccagggga ccaagctgga gatcaaac                                        328

<210> SEQ ID NO 45
<211> LENGTH: 322
<212> TYPE: DNA
<213> ORGANISM: Homo sapiens
<220> FEATURE:
<221> NAME/KEY: misc_feature
<222> LOCATION: (291)..(291)
<223> OTHER INFORMATION: n is a, c, g, or t

<400> SEQUENCE: 45
gagctcgtga tgacacagtc tccatcctca ctgtctgcat ctgtaggaga cagagtcacc      60
atcacttgtc gggcgagtca gggcattagc aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatagtt acccgatcac nttcggccaa    300
gggaccaagg tggaaatcaa ac                                              322

<210> SEQ ID NO 46
<211> LENGTH: 328
<212> TYPE: DNA
<213> ORGANISM: Homo sapiens

<400> SEQUENCE: 46
gagctcgtga tgacccagtc tccatcctcc ctgtctgcat ctgtaggaga cagagtcacc      60
atcacttgcc gggcaagtca gaccattagc aactatttaa attggtatca gcagaaacca    120
gggaaagccc ctaagctcct gatctatggt gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctccgac gtacactttt    300
ggccagggga ccaagctgga gatcaaac                                        328

<210> SEQ ID NO 47
<211> LENGTH: 337
<212> TYPE: DNA
<213> ORGANISM: Homo sapiens

<400> SEQUENCE: 47
gagctcgtga tgacccagtc tccactctcc ctgcccgtca cccttggaga gccggcctcc     60
atctcctgca ggtctagtca gagcctccag cagagtaatg acacaactta tttgaattgg    120
tacctgcaga agccaggcca gtctccacag ttcctgatcc acttgggttc taatcgggcc    180
tccggggtcc ctgacaggtt cagtggcagt ggatcaggca cagatttac actgaaaatc     240 agcagagtgg aggctgagga tgttggggtt tattactgca tgcaggctct acaaaccccg    300
ctcactttcg gcggagggac caaggtggaa atcaaac                              337
```

<210> SEQ ID NO 48
<211> LENGTH: 322
<212> TYPE: DNA
<213> ORGANISM: Homo sapiens

<400> SEQUENCE: 48
gagctcgtga tgacccagtc tccatcctcc ctgtctgcat ctgtaggaga cagaatcacc    60
atcacttgcc aggcgagtca ggacattggc acctctttaa attggtatca acagagacca   120
gggagagccc ctacagtcct gatctatgat gcatccaatt tgcaaacagg gtcccgtca    180 aggttcagtg aagtggatc tgggacacat tttactttca ccatcagcag cctgcagtct    240
gaagatattg caacatatca ctgtcaacag tatcataatg tcctgtacag ttttggccag    300
gggaccaaac tggagatcaa gc                                             322

<210> SEQ ID NO 49
<211> LENGTH: 325
<212> TYPE: DNA
<213> ORGANISM: Homo sapiens

<400> SEQUENCE: 49
gagctcgtga tgacccagtc tccatcctcc ctgtctgcat ctgtaggaga cagagtcacc    60
atcacttgcc gggcaagtca gaaccttaga aatgatttag actctggta tcagcagaaa    120 ccagggaaag cccctaacct cctgatctat ggtgcatcca gtttacaaag tggggtccca    180
tcaaggttca gcggcggtgg gtctggcaca gatttcactc tcaccatcag cagcctgcag    240
cctgaagatt ttgcaactta ttactgtcta caggattaca attacccgtg gacgttcggc    300
caagggacca aggtggagat caaac                                          325

<210> SEQ ID NO 50
<211> LENGTH: 322
<212> TYPE: DNA
<213> ORGANISM: Homo sapiens
<220> FEATURE:
<221> NAME/KEY: misc_feature
<222> LOCATION: (288)..(288)
<223> OTHER INFORMATION: n is a, c, g, or t

<400> SEQUENCE: 50
gagctcgtga tgacccagtc tccatcctcc ctgtctgcgt ctattgggaa cagagtcacc    60
atcacttgcc aggcgagtca ggacattggc acctctttaa attggtatca ccagaaacca   120
gggaaagccc ctaacctcct gatctacggt gcatccagtt tgcaaagtgg ggtcccctca    180
aggttcaatg gcagtggatc tgggacagat ttcactctca ccatcaccag tctgcaacct    240
gaggattttg cagcttacta ctgtcaacag agtttcagtg tccctacnac ttttggccag    300
gggaccaagc tggagatcac gc                                             322

<210> SEQ ID NO 51
<211> LENGTH: 321
<212> TYPE: DNA
<213> ORGANISM: Homo sapiens

<400> SEQUENCE: 51
gagctcgtga tgacccagtc tccatcctcc gtgtctgcgt ctcctggtga cagagtcact    60
atttcttgcc gggcaagtga gaccgttaat acatatctca actggtacca acaaaaacag   120
ggagaggccc ctaaagtcct aatctactct gcatccactt tgcaaagaga cgtcccgtcg   180
aggttcagtg gcagtggatc tgggacagat ttcactctca ccatcaccaa tgtacagcct   240

```
gacgattttg caacttacta ttgtcaacag agttatttaa cccctctcac tttcggcggc      300
gggaccaggg tcgatctccg a                                                321
```

<210> SEQ ID NO 52
<211> LENGTH: 321
<212> TYPE: DNA
<213> ORGANISM: Homo sapiens

<400> SEQUENCE: 52

```
gagctcgtga tgacccagtc tccatcctcc ctgtctgcgt ctcctggtga cagggtcact       60
atttcttgcc gggcaagtga gaccgttaat acatatctca actggtacca acaaaaacag      120
ggggaggccc ctaaagtcct gatctactct gcatccactt gcaaagaga cgtcccgtcg       180 aggttcagtg gcagtggatc tgggacagat ttcactctca ccatcaccaa tctgcagcct      240
gaagattttg caacttacta ttgtcaacag agttatttaa cccctctcac tttcggcggc      300
gggaccaagg tggatctcaa a                                                321
```

<210> SEQ ID NO 53
<211> LENGTH: 321
<212> TYPE: DNA
<213> ORGANISM: Homo sapiens

<400> SEQUENCE: 53

```
gagctcgtga tgacccagtc tccatccacc ctgtctgcgt ctcttggaga cagagtcact       60
atttcttgcc gggcaagtga gaccattaag acatatttaa attggtacca acaaaaacaa      120
ggagaggccc ctaaggtcct gatctcttca gcatccactt gcaaagaga cgtctcatcg       180 aggttcagtg gcagtgggtc tgggacagat ttcactctca ccatcaacaa tctgcagcct      240
gaagattttg caacttacta ctgtcagcag agttacacta cccctctcac ttttggcgga      300
gggaccaagg tcgatctcaa a                                                321
```

<210> SEQ ID NO 54
<211> LENGTH: 321
<212> TYPE: DNA
<213> ORGANISM: Homo sapiens

<400> SEQUENCE: 54

```
gagctcgtga tgacccagtc tccatcctcc ctgtctgcgt ctcttggaga cagagtcact       60
atttcttgcc gggcaagtca gaccattgat acatatttaa attggtacca accaaaacca      120
ggagaggccc ctaaggtcct gatccattct gcatccactt gccaagaga ggtcccatcg       180 aggttcagtg gcagtggatc tgggacagat ttcactctca ccatcaccaa tctgcagcct      240
gaagattttg caacttacta ctgtcaacag agttttacaa cccctctcac tttcggcgga      300
gggaccaagg tggatctcaa a                                                321
```

<210> SEQ ID NO 55
<211> LENGTH: 321
<212> TYPE: DNA
<213> ORGANISM: Homo sapiens

<400> SEQUENCE: 55

```
gagctcgtga tgacccagtc tccatccacc ctgtctgcgt ctcttggaga cagagtcact       60
atttcttgcc gggcaagtga gaccattaag acatatttaa attggtacca acaaaaacaa      120
ggagaggccc ctaaggtcct gatctctgca gcatccactt gcaaagaga cgtctcatcg       180 aggttcagtg gcagtgggtc tgggacagat ttcactctca ccatcaacaa tctgcagcct      240
```

```
gaagattttg caacttacta ctgtcagcag agttacacta cccctctcac tttcggcgga    300
gggaccaagg tcgatctcaa a                                               321

<210> SEQ ID NO 56
<211> LENGTH: 321
<212> TYPE: DNA
<213> ORGANISM: Homo sapiens

<400> SEQUENCE: 56
gagctcgtga tgacccagtc tccatcctcc ctgtctgcgt ctcttggaga cagagtcact     60
atttcttgcc gggcaagtca gaccatcaat tcaaatttaa attggtatca accaaaacca    120
ggagaggccc ctaaggtcct gatctctgca gcatccagtt tgcaaagaga agtcccatcg    180
aggttcagtg gcagtggatc tgggacagat ttcactctca ccatcagcaa tctgcagcct    240
gaagattttg caacttacta ctgtcagcag agttacacta cccctctcac tttcggcggt    300
gggaccaagg tggatctcaa a                                               321

<210> SEQ ID NO 57
<211> LENGTH: 321
<212> TYPE: DNA
<213> ORGANISM: Homo sapiens

<400> SEQUENCE: 57
gagctcgtga tgacccagtc tccatcctcc ctgtctgcat ctgtaggaga caaagtcacc     60
atcacttgcc gggcaagtca gagcattagc aactatttaa attggtatca gcagaaacca    120
gggaaagccc ctaaactcct gatctctgct gcatccagtt tgcaaagtgt ggtcccatca    180
aggttcagtg gcagtggatc tgcacggat ttcactctca ccatcagcgg tctacaacct     240
gaagattttg caacctacta ctgtcagcag agttacaata cccctaacac tttcggcccc    300
gggaccaaag tggatatcag a                                               321

<210> SEQ ID NO 58
<211> LENGTH: 339
<212> TYPE: DNA
<213> ORGANISM: Homo sapiens

<400> SEQUENCE: 58
gagctcgtga tgacccagtc tccagactcc ttggctgtgt ctctgggcga gagggccacc     60
atcaactgca gtccagcca gaatctttta tacagcgtca acaataaaaa ctacatagct     120
tggttccagc agaaaccagg acagccgcct aagttgctca tttactgggc atctatccgg    180
gaatccgggg tccctgaccg attcagtggc agcggatctg agacagattt cactctcacc    240
atcagcagcc tgcaggctga agatgtgca gtttattatt gtcagcaata ttctggtttt     300
tcgtggacat tcggccaagg gaccaaggtg gaaatcaaa                            339

<210> SEQ ID NO 59
<211> LENGTH: 141
<212> TYPE: DNA
<213> ORGANISM: Homo sapiens

<400> SEQUENCE: 59
gggctgagag caaccttcag tagctatagc aaccgccagg ctggggagtc atccattagt     60
agtagtagtt acatatacta cgcagactca gtgaagggcc gaaccgccaa ctcactgctg    120
caaaacagcg aggctgtgta c                                               141

<210> SEQ ID NO 60
```

```
<211> LENGTH: 141
<212> TYPE: DNA
<213> ORGANISM: Homo sapiens

<400> SEQUENCE: 60
gagctaagaa ttacctttaa tacctacaat aatcgtcagc ctggagaagc ttccataaca      60
gcgactagcc acacagagta cggaagctcc gttgcgggac gcaccaccaa gtctcttcta     120
gacacccgtg aagcactttt t                                                141

<210> SEQ ID NO 61
<211> LENGTH: 141
<212> TYPE: DNA
<213> ORGANISM: Homo sapiens

<400> SEQUENCE: 61
gagctaagaa ttacctttaa tacctacaat aatcgtcagc ctggagaagc ttcaataaca      60
gcgactagcc acacagagta cggaggctcc gttgcgggac gcaccgccaa gtctcttcta     120
gacacccgtg aagcactttt t                                                141

<210> SEQ ID NO 62
<211> LENGTH: 141
<212> TYPE: DNA
<213> ORGANISM: Homo sapiens

<400> SEQUENCE: 62
gagctaaggc ttacctttaa tacctacaat aatcgtcagc ctggagaagc ttcaataaca      60
gcgactagcc acacagagta cggaggctcc gttgcgggac gcaccaccaa gtctcttcta     120
gacacccgcg aagcactttt t                                                141

<210> SEQ ID NO 63
<211> LENGTH: 141
<212> TYPE: DNA
<213> ORGANISM: Homo sapiens

<400> SEQUENCE: 63
gaccgaaggg ttacctttaa cacctacaat aatcgtcagc ctggagaagc ttcaataacg      60
tcgactagcc atacagagta cggaggctcc gttgcgggcc gcaccaccaa gtctcttctg     120
gacacccgtg aggcactttt t                                                141

<210> SEQ ID NO 64
<211> LENGTH: 141
<212> TYPE: DNA
<213> ORGANISM: Homo sapiens

<400> SEQUENCE: 64
gagctaagaa ttactttaa tacctacaat aatcgtcaaa ctggagaggc atcaataagt      60
acgactagcc acacagagta cacagactcc gttgcggggc gcaccaccaa gtctcttcta     120
gacaccagcg aagcacttta t                                                141

<210> SEQ ID NO 65
<211> LENGTH: 141
<212> TYPE: DNA
<213> ORGANISM: Homo sapiens

<400> SEQUENCE: 65
gagctaagag ttacgtttaa cacctacaac aatcgtcagc ctggcgaggc ctcaataaca      60
acgactagcc atacagagta tggaggctct gttgcggagc ggagcaccaa gtccctgcta     120
```

```
gacacccgtg aagcactttt t                                            141

<210> SEQ ID NO 66
<211> LENGTH: 132
<212> TYPE: DNA
<213> ORGANISM: Homo sapiens

<400> SEQUENCE: 66
tccctggcag taggaagaac catcactcag agcattagca gctatttaaa ttatcagcag    60
ccagggaaaa agctcctgta tgctagtcaa agtgggccat caggaagcag tctgcaagaa   120
taccaataca gt                                                      132

<210> SEQ ID NO 67
<211> LENGTH: 132
<212> TYPE: DNA
<213> ORGANISM: Homo sapiens

<400> SEQUENCE: 67
tccgtggcgc ctggtagaac tatttctgag accgttaata catatctcaa ctaccaacaa    60
cagggagaga aagtcctata ctctactcaa agagacccgt cgggaaccaa tgtacaggac   120
tatcaatatt ta                                                      132

<210> SEQ ID NO 68
<211> LENGTH: 132
<212> TYPE: DNA
<213> ORGANISM: Homo sapiens

<400> SEQUENCE: 68
tccctggcgc ctggtaggac tatttctgag accgttaata catatctcaa ctaccaacaa    60 caggggagaga aagtcctgta ctctactcaa agagacccgt cgggaaccaa tctgcaggaa  120
tatcaatatt ta                                                      132

<210> SEQ ID NO 69
<211> LENGTH: 132
<212> TYPE: DNA
<213> ORGANISM: Homo sapiens

<400> SEQUENCE: 69
accctggcgc ttggaagaac tatttctgag accattaaga catatttaaa ttaccaacaa    60
caaggagaga aggtcctgtc ttcaactcaa agagactcat cggggaacaa tctgcaggaa   120
taccagtaca ct                                                      132

<210> SEQ ID NO 70
<211> LENGTH: 132
<212> TYPE: DNA
<213> ORGANISM: Homo sapiens

<400> SEQUENCE: 70
tccctggcgc ttggaagaac tatttctcag accattgata catatttaaa ttaccaacca    60
ccaggagaga aggtcctgca ttctactcca agagagccat cgggaaccaa tctgcaggaa   120
taccaattta ca                                                      132

<210> SEQ ID NO 71
<211> LENGTH: 132
<212> TYPE: DNA
<213> ORGANISM: Homo sapiens

<400> SEQUENCE: 71
```

```
acctggcgc ttggaagaac tatttctgag accattaaga catatttaaa ttaccaacaa      60
caaggagaga aggtcctgtc tgcaactcaa agagactcat cggggaacaa tctgcaggaa     120
taccagtaca ct                                                         132
```

<210> SEQ ID NO 72
<211> LENGTH: 132
<212> TYPE: DNA
<213> ORGANISM: Homo sapiens

<400> SEQUENCE: 72

```
tccctggcgc ttggaagaac tatttctcag accatcaatt caaatttaaa ttatcaacca      60
ccaggagaga aggtcctgtc tgcaagtcaa agagaaccat cgggaagcaa tctgcaggaa     120
taccagtaca ct                                                         132
```

<210> SEQ ID NO 73
<211> LENGTH: 47
<212> TYPE: PRT
<213> ORGANISM: Homo sapiens

<400> SEQUENCE: 73

Gly Leu Arg Ala Thr Phe Ser Ser Tyr Ser Asn Arg Gln Ala Gly Glu
1               5                   10                  15

Ser Ser Ile Ser Ser Ser Tyr Ile Tyr Tyr Ala Asp Ser Val Lys
            20                  25                  30

Gly Arg Thr Ala Asn Ser Leu Leu Gln Asn Ser Glu Ala Val Tyr
        35                  40                  45

<210> SEQ ID NO 74
<211> LENGTH: 47
<212> TYPE: PRT
<213> ORGANISM: Homo sapiens

<400> SEQUENCE: 74

Glu Leu Arg Ile Thr Phe Asn Thr Tyr Asn Asn Arg Gln Pro Gly Glu
1               5                   10                  15

Ala Ser Ile Thr Ala Thr Ser His Thr Glu Tyr Gly Ser Val Ala
            20                  25                  30

Gly Arg Thr Thr Lys Ser Leu Leu Asp Thr Arg Glu Ala Leu Phe
        35                  40                  45

<210> SEQ ID NO 75
<211> LENGTH: 47
<212> TYPE: PRT
<213> ORGANISM: Homo sapiens

<400> SEQUENCE: 75

Glu Leu Arg Ile Thr Phe Asn Thr Tyr Asn Asn Arg Gln Pro Gly Glu
1               5                   10                  15

Ala Ser Ile Thr Ala Thr Ser His Thr Glu Tyr Gly Gly Ser Val Ala
            20                  25                  30

Gly Arg Thr Ala Lys Ser Leu Leu Asp Thr Arg Glu Ala Leu Phe
        35                  40                  45

<210> SEQ ID NO 76
<211> LENGTH: 47
<212> TYPE: PRT
<213> ORGANISM: Homo sapiens

<400> SEQUENCE: 76

Glu Leu Arg Leu Thr Phe Asn Thr Tyr Asn Asn Arg Gln Pro Gly Glu

```
                1               5                   10                  15
Ala Ser Ile Thr Ala Thr Ser His Thr Glu Tyr Gly Gly Ser Val Ala
                20                  25                  30

Gly Arg Thr Thr Lys Ser Leu Leu Asp Thr Arg Glu Ala Leu Phe
                35                  40                  45

<210> SEQ ID NO 77
<211> LENGTH: 47
<212> TYPE: PRT
<213> ORGANISM: Homo sapiens

<400> SEQUENCE: 77

Asp Arg Arg Val Thr Phe Asn Thr Tyr Asn Asn Arg Gln Pro Gly Glu
1               5                   10                  15

Ala Ser Ile Thr Ser Thr Ser His Thr Glu Tyr Gly Gly Ser Val Ala
                20                  25                  30

Gly Arg Thr Thr Lys Ser Leu Leu Asp Thr Arg Glu Ala Leu Phe
                35                  40                  45

<210> SEQ ID NO 78
<211> LENGTH: 47
<212> TYPE: PRT
<213> ORGANISM: Homo sapiens

<400> SEQUENCE: 78

Glu Leu Arg Ile Thr Phe Asn Thr Tyr Asn Asn Arg Gln Thr Gly Glu
1               5                   10                  15

Ala Ser Ile Ser Thr Thr Ser His Thr Glu Tyr Thr Asp Ser Val Ala
                20                  25                  30

Gly Arg Thr Thr Lys Ser Leu Leu Asp Thr Ser Glu Ala Leu Tyr
                35                  40                  45

<210> SEQ ID NO 79
<211> LENGTH: 47
<212> TYPE: PRT
<213> ORGANISM: Homo sapiens

<400> SEQUENCE: 79

Glu Leu Arg Val Thr Phe Asn Thr Tyr Asn Asn Arg Gln Pro Gly Glu
1               5                   10                  15

Ala Ser Ile Thr Thr Thr Ser His Thr Glu Tyr Gly Gly Ser Val Ala
                20                  25                  30

Glu Arg Ser Thr Lys Ser Leu Leu Asp Thr Ser Glu Ala Leu Phe
                35                  40                  45

<210> SEQ ID NO 80
<211> LENGTH: 44
<212> TYPE: PRT
<213> ORGANISM: Homo sapiens

<400> SEQUENCE: 80

Ser Leu Ala Val Gly Arg Thr Ile Thr Gln Ser Ile Ser Ser Tyr Leu
1               5                   10                  15

Asn Tyr Gln Gln Pro Gly Lys Lys Leu Leu Tyr Ala Ser Gln Ser Gly
                20                  25                  30

Pro Ser Gly Ser Ser Leu Gln Glu Tyr Gln Tyr Ser
                35                  40

<210> SEQ ID NO 81
<211> LENGTH: 44
<212> TYPE: PRT
```

<213> ORGANISM: Homo sapiens

<400> SEQUENCE: 81

Ser Val Ala Pro Gly Arg Thr Ile Ser Glu Thr Val Asn Thr Tyr Leu
1               5                   10                  15

Asn Tyr Gln Gln Gln Gly Glu Lys Val Leu Tyr Ser Thr Gln Arg Asp
                20                  25                  30

Pro Ser Gly Thr Asn Val Gln Asp Tyr Gln Tyr Leu
            35                  40

<210> SEQ ID NO 82
<211> LENGTH: 44
<212> TYPE: PRT
<213> ORGANISM: Homo sapiens

<400> SEQUENCE: 82

Ser Leu Ala Pro Gly Arg Thr Ile Ser Glu Thr Val Asn Thr Tyr Leu
1               5                   10                  15

Asn Tyr Gln Gln Gln Gly Glu Lys Val Leu Tyr Ser Thr Gln Arg Asp
                20                  25                  30

Pro Ser Gly Thr Asn Leu Gln Glu Tyr Gln Tyr Leu
            35                  40

<210> SEQ ID NO 83
<211> LENGTH: 44
<212> TYPE: PRT
<213> ORGANISM: Homo sapiens

<400> SEQUENCE: 83

Thr Leu Ala Leu Gly Arg Thr Ile Ser Glu Thr Ile Lys Thr Tyr Leu
1               5                   10                  15

Asn Tyr Gln Gln Gln Gly Glu Lys Val Leu Ser Ser Thr Gln Arg Asp
                20                  25                  30

Ser Ser Gly Asn Asn Leu Gln Glu Tyr Gln Tyr Thr
            35                  40

<210> SEQ ID NO 84
<211> LENGTH: 44
<212> TYPE: PRT
<213> ORGANISM: Homo sapiens

<400> SEQUENCE: 84

Ser Leu Ala Leu Gly Arg Thr Ile Ser Gln Thr Ile Asp Thr Tyr Leu
1               5                   10                  15

Asn Tyr Gln Pro Pro Gly Glu Lys Val Leu His Ser Thr Pro Arg Glu
                20                  25                  30

Pro Ser Gly Thr Asn Leu Gln Glu Tyr Gln Phe Thr
            35                  40

<210> SEQ ID NO 85
<211> LENGTH: 44
<212> TYPE: PRT
<213> ORGANISM: Homo sapiens

<400> SEQUENCE: 85

Thr Leu Ala Leu Gly Arg Thr Ile Ser Glu Thr Ile Lys Thr Tyr Leu
1               5                   10                  15

Asn Tyr Gln Gln Gln Gly Glu Lys Val Leu Ser Ala Thr Gln Arg Asp
                20                  25                  30

Ser Ser Gly Asn Asn Leu Gln Glu Tyr Gln Tyr Thr
            35                  40

```
<210> SEQ ID NO 86
<211> LENGTH: 44
<212> TYPE: PRT
<213> ORGANISM: Homo sapiens

<400> SEQUENCE: 86

Ser Leu Ala Leu Gly Arg Thr Ile Ser Gln Thr Ile Asn Ser Asn Leu
1               5                   10                  15

Asn Tyr Gln Pro Pro Gly Glu Lys Val Leu Ser Ala Ser Gln Arg Glu
            20                  25                  30

Pro Ser Gly Ser Asn Leu Gln Glu Tyr Gln Tyr Thr
            35                  40
```